(12) United States Patent
Suthanthiran et al.

(10) Patent No.: US 9,746,479 B2
(45) Date of Patent: Aug. 29, 2017

(54) METHODS AND COMPOSITIONS TO PREDICT AND DETECT ACUTE REJECTION

(75) Inventors: Manikkam Suthanthiran, Scarsdale, NY (US); Abraham Shaked, Wynnewood, PA (US)

(73) Assignees: Cornell University, Ithaca, NY (US); The Trustees of the University of Pennsylvania, Philadelphia, PA (US)

(*) Notice: Subject to any disclaimer, the term of this patent is extended or adjusted under 35 U.S.C. 154(b) by 58 days.

(21) Appl. No.: 13/583,750

(22) PCT Filed: Mar. 9, 2011

(86) PCT No.: PCT/US2011/027754
§ 371 (c)(1),
(2), (4) Date: Sep. 10, 2012

(87) PCT Pub. No.: WO2011/112719
PCT Pub. Date: Sep. 15, 2011

(65) Prior Publication Data
US 2013/0012860 A1    Jan. 10, 2013

Related U.S. Application Data

(60) Provisional application No. 61/312,151, filed on Mar. 9, 2010, provisional application No. 61/444,354, filed on Feb. 18, 2011.

(51) Int. Cl.
*C12Q 1/68* (2006.01)
*C12P 19/34* (2006.01)
*G01N 33/68* (2006.01)

(52) U.S. Cl.
CPC ....... *G01N 33/6893* (2013.01); *C12Q 1/6883* (2013.01); *C12Q 2600/118* (2013.01); *C12Q 2600/158* (2013.01); *G01N 2800/245* (2013.01)

(58) Field of Classification Search
CPC ............... C12Q 1/6883; C12Q 1/6809; C12Q 2600/158; C12Q 2600/106; C12Q 1/6876; C12Q 1/6895; G01N 2800/245; G01N 33/6893
See application file for complete search history.

(56) References Cited

U.S. PATENT DOCUMENTS

| 6,187,534 B1 | 2/2001 | Strom |
| 6,900,015 B2 | 5/2005 | Avihingsanon et al. |
| 2001/0051344 A1 | 12/2001 | Shalon et al. |
| 2004/0053284 A1 | 3/2004 | Andrus et al. |
| 2005/0175539 A1 | 8/2005 | Morishita et al. |
| 2006/0088836 A1 | 4/2006 | Wohlgemuth |
| 2007/0010759 A1 | 1/2007 | Parsonnet et al. |
| 2007/0031890 A1 | 2/2007 | Wohlgemuth |
| 2008/0131441 A1 | 6/2008 | Suthanthiran |
| 2010/0303806 A1 | 12/2010 | Harvey |
| 2012/0101001 A1 | 4/2012 | Suthanthiran |
| 2014/0213533 A1 | 7/2014 | Suthanthiran et al. |

FOREIGN PATENT DOCUMENTS

| CN | 1654637 A | 8/2005 |
| EP | 0534858 A1 | 3/1993 |
| WO | WO-2008079303 A2 | 7/2008 |
| WO | WO-2010105275 A2 | 9/2010 |
| WO | WO-2011/112719 A1 | 9/2011 |

OTHER PUBLICATIONS

Hsieh M.-F. et al. J Immunol 2006; 177:1855-1863.*
Flechner, S. M. et al. American Journal of Transplantation 2004; 4: 1475-1489.*
Kotsch, K. et al. Transplantation, vol. 77, 1866-1875, No. 12, Jun. 27, 2004.*
Tatapudi, R. R. et al. Kidney International, vol. 65 (2004), pp. 2390-2397.*
Aquino-Dias, E. C. et al. Kidney International (2008) 73, 877-884.*
Cobb, J. P. et al. Crit Care Med 2002 vol. 30, No. 12, pp. 2711-2721.*
Cheung, V. G. et al. Nature Genetics, vol. 33 (Mar. 2003), pp. 422-425.*
Chen, G. et al. Molecular & Cellular Proteomics 1.4 (2002) pp. 304-313.*
Hoshikawa, Y. et al. Physiol Genomics 12: 209-219, 2003.*
Veronese F. et al. American Journal of Transplantation 2007; 7: 914-922.*
Simon, T. et al. Transplantation (2004) vol. 77, No. 10, pp. 1589-1595, May 27, 2004.*
Simon T. et al. American Journal of Transplantation 2003; 3: 1121-1127.*
Kotsch K. et al. Transplantation, vol. 77, p. 1866-1875, No. 12, Jun. 27, 2004.*
Anglicheau, D. et al. Transplantation, vol. 86, No. 2, Jul. 27, 2008, p. 192-199.*
International Search Report PCT/US2011/27754, dated Apr. 30, 2011.
Written Opinion of the International Searching Authority PCT/US2011/27754, dated Apr. 30, 2011.
"International Application Serial No. PCT/US11/27754, International Preliminary Report on Patentability dated Sep. 11, 2012", 6 pgs.
Afaneh, C., et al., "Urinary Cell Levels of mRNA for OX40, OX4OL, PD-1, PD-L1 or PD-L2 and Acute Rejection of Human Renal Allografts", *Transplantation*, 90(12), (2010), 14 pgs.
Anglicheau, D., et al., "Noninvasive Prediction of Organ Graft Rejection and Outcome Using Gene Expression Patterns", *Transplantation*, 86(2), (2008), 15 pgs.

(Continued)

*Primary Examiner* — Stephen Kapushoc
(74) *Attorney, Agent, or Firm* — Schwegman Lundberg & Woessner, P.A.

(57) ABSTRACT

In some embodiments, a method to detect acute rejection in allograft from is described. In some embodiments, a method to anticipate an episode of acute rejection in allografts is also described. In some embodiments, a kit for detecting or predicting acute transplant rejection of a transplanted organ is described.

7 Claims, 6 Drawing Sheets

(56) References Cited

OTHER PUBLICATIONS

Dadhania, D., et al., "Molecular signatures of urinary cells distinguish acute rejection of renal allografts from urinary tract infection", (Abstract Only), *Transplantation*, 75(10), 1752-1754, (2003), 1 pg.

Ding, R., et al., "CD102 mRNA Levels in Urinary Cells Predict Acute Rejection of Renal Allografts", *Transplantation*, 75(8), (2003), 1307-1312.

Ding, R., et al., "Noninvasive Diagnosis of BK Virus Nephritis by Measurement of Messenger RNA for BK Virus VP1 in Urine", *Transplantation*, 74(7), (2002), 987-994.

Gibson, U. E. M., et al., "A Novel Method for Real Time Quantitative RT-PCR", *Genome Research*, 6, (1996), 995-1001.

Heid, C. A., et al., "Real Time Quantitative PCR", *Genome Research*, 6, (1996), 986-994.

Li, B., et al., "Noninvasive Diagnosis of Renal-Allograft Rejection by Measurement of Messenger RNA for Perforin arid Granzyme B in Urine", *The New England Journal of Medicine*, 344(13), (2001), 947-954.

Muthukumar, T., et al., "Messenger RNA for FOXP3 in the Urine of Renal-Allograft Recipients", *New England Journal of Medicine*, 353(22), (2005), 2342-2351.

Muthukumar, T., et al., "Serine Proteinase Inhibitor-9, an Endogenous Blocker of Granzyme B/Perforin Lytic Pathway, is Hyperexpressed During Acute Rejection of Renal Allografts", *Transplantation*, 75(9), (2003), 1565-1570.

Prashar, Y., et al., "Analysis of differential gene expression by display of 3' end restriction fragments of cDNA's", *Proc. Natl. Acad. Sci. USA*, 93, (Jan. 1996), 659-663.

Tatapudi, R. R., et al., "Noninvasive detection of renal allograft inflammation by measurements of mRNA for IP-10 and CXCR3 in urine", *Kidney International*, 65(6), (2004), 2390-2397.

Tyagi, S., et al., "Beacons of Light", Nature Biotechnology, 24(3), (1996), 303-304.

Velculescu, V. E., et al., "Serial Analysis of Gene Expression", *Science*, 270(5235), (1995), 484-487.

Zhang, Z., et al., "A Linear Regression Framework for Receiver Operating Characteristics (ROC) Curve Analysis", University of Washington Biostatistics Working Paper Series, (2005), 23 pgs.

"U.S. Appl. No. 13/256,422, Response filed Nov. 13, 2014 to Non Final Office Action mailed Aug. 13, 2014", 15 pgs.

"Chinese Application Serial No. 201080021368.6, Office Action mailed Jul. 3, 2014", (w/ English Translation), 25 pgs.

"Chinese Application Serial No. 201080021368.6, Response filed Sep. 18, 2014 to Office Action mailed Jul. 3, 2014", (w/ English Translation of Amended Claims), 23 pgs.

"International Application Serial No. PCT/US2010/027361, International Search Report mailed Nov. 4, 2010", 6 pgs.

Chang, Alexander T., et al., "The role of antibodies in transplantation", *Transplantation Reviews*, 23(4), (2009), 191-198.

Kalaaji, M., et al., "Glomerular apoptotic nucleosomes are central target structures for nephritogenic antibodies in human SLE nephritis", *Kidney International*, 71(7), (2007), 664-672.

"U.S. Appl. No. 13/256,422, Advisory Action mailed Mar. 23, 2015", 3 pgs.

"U.S. Appl. No. 13/256,422, Advisory Action mailed Apr. 27, 2016", 4 pgs.

"U.S. Appl. No. 13/256,422, Advisory Action mailed May 25, 2016", 3 pgs.

"U.S. Appl. No. 13/256,422, Examiner Interview Summary mailed Jan. 25, 2016", 3 pgs.

"U.S. Appl. No. 13/256,422, Final Office Action mailed Feb. 19, 2016", 17 pgs.

"U.S. Appl. No. 13/256,422, Final Office Action mailed Dec. 18, 2014", 19 pgs.

"U.S. Appl. No. 13/256,422, Non Final Office Action mailed Oct. 5, 2016", 14 pgs.

"U.S. Appl. No. 13/256,422, Non Final Office Action mailed Oct. 22, 2015", 16 pgs.

"U.S. Appl. No. 13/256,422, Notice of Allowance mailed Feb. 21, 2017", 10 pgs.

"U.S. Appl. No. 13/256,422, Response filed Jan. 5, 2017 to Non Final Office Action mailed Oct. 5, 2016", 13 pgs.

"U.S. Appl. No. 13/256,422, Response filed Jan. 21, 2016 to Non Final Office Action mailed Oct. 22, 2015", 13 pgs.

"U.S. Appl. No. 13/256,422, Response filed Mar. 17, 2015 to Final Office Action mailed Dec. 18, 2014", 14 pgs.

"U.S. Appl. No. 13/256,422, Response filed Apr. 19, 2016 to Final Office Action mailed Feb. 19, 2016", 14 pgs.

"U.S. Appl. No. 13/256,422, Response filed May 16, 2016 to Final Office Action mailed Feb. 19, 2016", 17 pgs.

"U.S. Appl. No. 14/170,132, Final Office Action mailed Aug. 9, 2016", 10 pgs.

"U.S. Appl. No. 14/170,132, Non Final Office Action mailed Jan. 29, 2016", 8 pgs.

"U.S. Appl. No. 14/170,132, Response filed Apr. 27, 2016 to Non Final Office Action mailed Jan. 29, 2016", 8 pgs.

"U.S. Appl. No. 14/170,132, Response filed Sep. 25, 2015 to Restriction Requirement mailed Jul. 28, 2015", 6 pgs.

"U.S. Appl. No. 14/170,132, Response filed Nov. 9, 2016 to Final Office Action mailed Aug. 9, 2016", 6 pgs.

"U.S. Appl. No. 14/170,132, Restriction Requirement mailed Jul. 28, 2015", 7 pgs.

"Chinese Application Serial No. 201080021368.6, Decision of Rejection mailed Aug. 6, 2015", (w/ English Summary), 8 pgs.

"Chinese Application Serial No. 201080021368.6, Office Action mailed Jan. 20, 2015", (w/ English Translation), 15 pgs.

"Chinese Application Serial No. 201080021368.6, Office Action mailed Dec. 21, 2016", With English Translation, 15 pgs.

"Chinese Application Serial No. 201080021368.6, Response filed Feb. 3, 2017 to Office Action mailed Dec. 21, 2016", With English Translation of Claims, 11 pgs.

"Chinese Application Serial No. 201080021368.6, Response filed Apr. 3, 2015 to Office Action mailed Jan. 20, 2015", (w/ English Translation of Claims), 19 pgs.

"European Application Serial No. 10751549.6, Extended European Search Report mailed Aug. 13, 2015", 9 pgs.

"European Application Serial No. 10751549.6, Office Action mailed Apr. 11, 2014", 3 pgs.

"U.S. Appl. No. 13/256,422, Non Final Office Action mailed Aug. 13, 2014", 22 pgs.

"U.S. Appl. No. 13/256,422, Preliminary Amendment filed Sep. 13, 2011", 9 pgs.

"U.S. Appl. No. 13/256,422, Response filed Jul. 17, 2014 to Restriction Requirement mailed Jun. 17, 2014", 11 pgs.

"U.S. Appl. No. 13/256,422, Restriction Requirement mailed Jun. 17, 2014", 8 pgs.

"Chinese Application Serial No. 201080021368.6, Office Action mailed Oct. 23, 2013", (w/ English Translation), 12 pgs.

"Chinese Application Serial No. 201080021368.6, Response filed Mar. 7, 2014 to Office Action mailed Oct. 23, 2013", 102 pgs.

"Chinese Application Serial No. 201080021368.6, Voluntary Amendment filed Jul. 18, 2013", (w/ English Translation of Claims), 29 pgs.

"European Application Serial No. EP10751549.6, Amendment filed Oct. 12, 2011", 7 pgs.

"*Homo sapiens* miRNAs (1872 sequences)", [online]. [retrieved on Feb. 25, 2014]. Retrieved from the Internet: <URL: http://www.mirbase.org/cgi-bin/mirna_summary.pl?org=hsa>, 48 pgs.

"International Application Serial No. PCT/US10/27361, International Search Report mailed Nov. 4, 2010", 6 pgs.

"International Application Serial No. PCT/US2010/027361, International Preliminary Report on Patentability mailed Feb. 27, 2014", 9 pgs.

"International Application Serial No. PCT/US2010/027361, Written Opinion mailed Nov. 4, 2010", 7 pgs.

"miRNA entry MI0000458 hsa-miR-148", [Online]. Retrived from Internet: <http://www.mirbase.org/cgi-bin/mirna_entry.pl?id=hsa-miR-142-5p, (Apr. 2010), 2 pgs.

(56) References Cited

OTHER PUBLICATIONS

"TaqMan(r) MicroRNA Assays and Arrays—Product Bulletin", (c) 2011 Life Technologies Corporation, 4 pgs.

Anglicheau, A., et al., "MicroRNA expression profiles predictive of human renal allograft status", Proc. Natl. Acad. Sci., USA, 106(13), (2009), 5330-5335.

Chan, et al., "Expression of Chemokine and Fibrosing Factor Messenger RNA in the Urinary Sediment of Patients With Lupus Nephritis.", Arthritis & Rheumatism, 50(9), (2004), 2882-2890.

Cobb, et al., "A role for Dicer in immune regulation", The Journal of Experimental Medicine 203(11), (2006), 2519-2527.

Dai, Y., et al., "Comprehensive analysis of microRNA expression patterns in renal biopsies of lupus nephritis patients", Rheumatol Int., vol. 29, 7, (2008), 749-754.

D'Cruz, "Antibodies to endothelial cells in systemic lupus erythematosus: a potential marker for nephritis and vasculitis.", Clin. expo Immunol 85, (1991), 254-261.

Ferry, et al., "Anti-cell surface endothelial antibodies in sera from cardiac and kidney transplant recipients : association with chronic rejection.", Transplant Immunology 5, (1997), 17-24.

Grandaliano, "Monocyte chemotactic peptide-1 expression and monocyte infiltration in acute renal transplant rejection", Transplantation, 63(3), (1997), 414-420.

Kroese, Mark, et al., "Genetic Tests and their Evaluation: Can we Answer the Key Questions?", Genetics in Medicine, vol. 6, No. 6, (2004), 475-480.

Lucentini, J., "Gene Association Studies Typically Wrong", The Scientist, vol. 18 No. 24, (Dec. 20, 2004), 20.

Raymond, C. K., et al., "Simple, quantitative primer-extension PCR assay for direct monitoring of microRNAs and short-interfering RNAs", RNA, 11, (2005), 1737-1744.

Sui, W., et al., "Microarray analysis of MicroRNA expression in acute rejection after renal transplantation", Transpl Immunol., 19(1), (Apr. 2008), 81-85.

Wu, et al., "miRNA Profiling of Naive, Effector and Memory CD8 T Cells", PLoS, 2(10)e 1020:1, (2007), 11 pgs.

\* cited by examiner

METHODS AND COMPOSITIONS TO PREDICT AND DETECT ACUTE REJECTION

This application is the national stage application of PCT/US2011/027754 which claims the benefit of the filing date of U.S. Provisional Application Ser. No. 61/312,151, filed Mar. 9, 2010, and U.S. Provisional Application Ser. No. 61/444,354, filed Feb. 18, 2011. These entire disclosures are hereby incorporated by reference into the present disclosure.

GOVERNMENT FUNDING

This invention was made with Government support under Grant Number 5U01AI063589-05S1 and 5U01AI063589-05 awarded by National Institute of Allergy and Infectious Diseases. The United States Government has certain rights in the invention.

BACKGROUND

Organ transplantation or the transfer of an organ from one human to another continues to rise throughout the world as the treatment of choice when an organ is irreversibly damaged and organ function is severely impaired. Organ transplantation is not without complications, not only from the transplant surgery itself, but also from the transplant recipient's own immune system and this process, if it happens suddenly, is called acute rejection.

For example, when acute rejection of a kidney transplant occurs, it manifests itself by a sudden deterioration in kidney transplant function, and about 30 percent of the transplant recipients experience an episode of acute rejection. Acute rejection can be associated with about a 20 percent reduction in the one-year survival rate of kidney grafts from a deceased donor, and the projected half-life is about four years shorter in patients who have had an episode of acute rejection compared to patients who have not had an episode of acute rejection.

Sometimes, acute rejection can result from the activation of recipient's T cells and/or B cells; the rejection primarily due to T cells is classified as T cell mediated acute rejection or acute cellular rejection (ACR) and the rejection in which B cells are primarily responsible is classified as antibody mediated acute rejection (AMR). Often times acute rejection of either type can result in the complete loss of transplant function and transplant failure.

In particular, for kidney transplants, an increase in the level of serum creatinine, a clinically used measure of kidney function, is often the first clinical indicator of acute rejection, and is currently the best surrogate marker of acute rejection of either type. However, this biomarker lacks sensitivity and specificity since graft dysfunction can occur due to a non-immunologic causes as well.

For example, two of the commonly used drugs in transplant recipients to prevent rejection, cyclosporine as well as tacrolimus, can cause kidney toxicity, and this complication is not readily identified solely on the basis of blood concentrations of cyclosporine/tacrolimus. In kidney transplant patients, the clinical importance of distinguishing acute rejection from cyclosporine/tacrolimus toxicity cannot be overemphasized since the treatment approaches are diametrically opposite. In one instance, continued administration of cyclosporine/tacrolimus for rejection is critical whereas, in the other instance, a reduction in dosage or discontinuation of cyclosporine/tacrolimus is indicated to prevent further kidney toxicity. Furthermore, deterioration in kidney function is not always available as a clinical clue to diagnose rejection because many of the kidney transplants suffer from acute (reversible) renal failure in the immediate post-transplantation period due to injury from organ procurement and the ex-vivo preservation procedures involved.

Currently, acute rejection is diagnosed by performing the invasive core needle biopsy procedure, which obtains a biopsy of the kidney graft. The histological features in the allograft biopsy is then observed. However, this invasive biopsy procedure is associated with complications such as bleeding, arteriovenous fistula, graft loss, and, in severe cases, even death.

Development of a noninvasive test either to anticipate an episode of acute rejection or to diagnose acute rejection without performing the transplant biopsy procedure is a major and an unmet goal in organ transplantation. The benefit of development of a noninvasive test to anticipate acute rejection is that rejection could be identified prior to organ injury and graft dysfunction and preemptive anti-rejection therapy can be started. Similarly, the benefit of diagnosing rejection with a noninvasive test is that the invasive biopsy procedure that can be associated with complications such as bleeding and even death of the patient could be avoided. Further, it would be beneficial to have a noninvasive test that can anticipate acute transplant rejection as well as serve as surrogates for the biopsy procedure. It would also be beneficial to provide a non-invasive test that provides information regarding the mechanisms responsible for acute rejection, and anti-rejection therapy can be customized to the specific biomarkers of the patient, and therefore, the "one size fits all" approach to treat all transplants the same way can be avoided. Therefore, there is a need for new methods and compositions for detecting acute transplant rejection. Non-invasive tests that predict acute rejection and its timeline would also be very useful.

SUMMARY

In certain embodiments, the inventors have made the surprising discoveries that it is possible to anticipate the future development of acute cellular rejection with a high degree of accuracy; and diagnose acute cellular rejection with a high degree of sensitivity and specificity without performing an organ transplant biopsy, by measuring the levels of expression of a small number of messenger RNAs (mRNAs) that encode the following protein(s): perforin, granzyme B, proteinase inhibitor-9 (PI-9), interferon inducing protein-10 (IP-10), FoxP3, TGF-beta-1, CXCR3, and/or CD3.

In certain embodiments, the amounts of mRNAs of perforin, granzyme B, proteinase inhibitor-9 (PI-9), interferon inducing protein-10 (IP-10), FoxP3, CD103, and/or CD3 are significantly higher in cells obtained from urine samples of patients undergoing acute rejection than in samples from patients not undergoing rejection. Surprisingly, weighted combinations of specific mRNAs from urine samples can identify acute rejection or predict its occurrence within a given time in the future.

In one embodiment, there is a method of diagnosing acute cellular rejection by obtaining a signature comprising a weighted combination of the amounts of mRNA of perforin, IP-10, Fox p3 and TGF-beta1 in a urine sample obtained from a transplant patient at the time of transplant biopsy, with weights based on a logistic regression model.

In another embodiment, there is a noninvasive method to anticipate the future development of acute cellular rejection of kidney transplants by measurement of messenger RNA (mRNA) in urine samples, collected in a longitudinal fashion, from the renal allograft recipients. A combination of levels of mRNAs for perforin, PI-9, IP-10, CXCR3, CD3 and granzyme B accurately distinguishes patients who will develop acute cellular rejection in the near future from those who will not develop acute cellular rejection. In particular, a weighted combination of mRNA levels of perforin and PI-9 in urine samples from transplant patients anticipates ACR 60 to 90 days prior to a performance of a transplant biopsy. Similarly, a weighted linear combination of perforin, 1P-10, CXCR3, and FoxP3 anticipates ACR 30 to 59 days prior to the performance of the transplant biopsy. Further, a weighted linear combination of perforin, PI-9, 1P-10, CXCR3, and CD3, are indicative of development of ACR in 15 to 29 days.

In certain embodiments, there is a method for detecting acute transplant rejection of a transplanted organ in a patient, the method comprising determining a level of gene expression of perforin, granzyme B, IP-10, CD3, FoxP3, CXCR3, CD103 and/or TGF-β1 in a sample from the patient; and comparing the level of gene expression to a baseline level of gene expression of perforin, granzyme B, IP-10, CD3, FoxP3, CXCR3, CD103 and/or TGF-β1, wherein upregulation of gene expression of perforin, granzyme B, IP-10, CD3, FoxP3, CXCR3, CD103 and/or TGF-β1 in the sample from the patient relative to the baseline level of gene expression indicates acute rejection of the transplanted organ. In certain embodiments, the gene expression is mRNA from urine cells from a kidney transplant patient.

In another embodiment, there is a method for predicting acute rejection of a transplanted organ in a patient, the method comprising determining a level of gene expression of perforin, granzyme B, IP-10, CD103, PI-9, CXCR3, CD3 and/or FoxP3 in a sample from the patient; and comparing the level of gene expression to a baseline level of gene expression of perforin, granzyme B, IP-10, CD103, PI-9, CXCR3, CD3 and/or FoxP3, wherein upregulation of gene expression of perforin, granzyme B, IP-10, CD103, PI-9, CXCR3, CD3 and/or FoxP3 in the sample relative to the baseline level of gene expression predicts acute rejection of the transplanted organ. In certain embodiments, the gene expression is mRNA from urine cells from a kidney transplant patient.

In yet another embodiment, there is a kit for detecting or predicting acute transplant rejection of a transplanted organ in a patient, the kit comprising: a urine sample preparation system and a plurality of polynucleotides that are configured to detect at least three genes selected from the group consisting of perforin, granzyme B, IP-10, CD3, FoxP3, CXCR3, CD103, TGF-β1, or PI-9.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying figures where:

DETAILED DESCRIPTION

Figure 1:
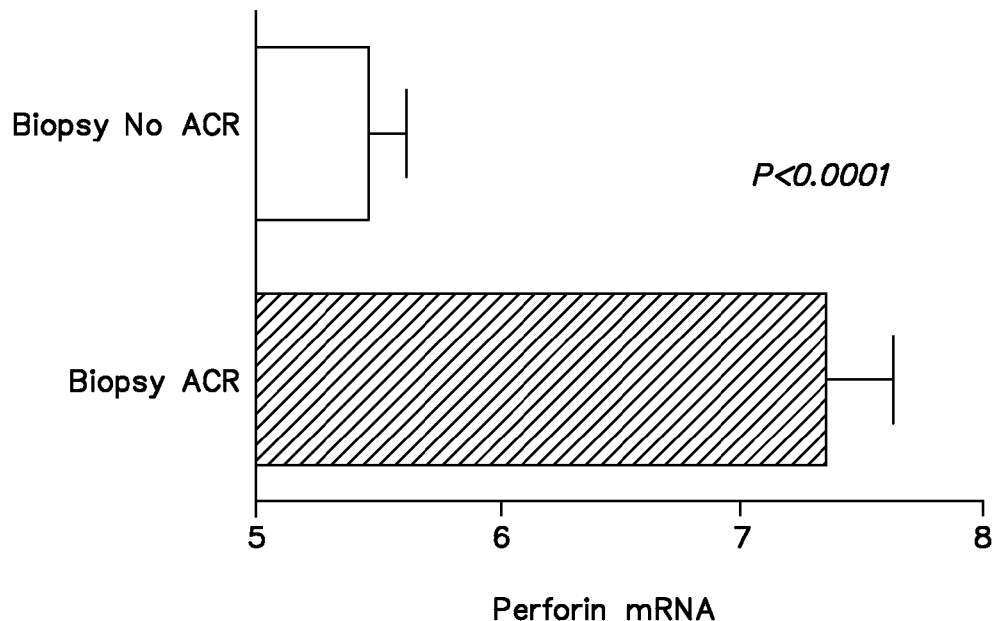
FIG. 1. Urinary Cell Perforin mRNA Levels are Diagnostic of Acute Cellular Rejection. A. "Biopsy ACR"=43 urine specimens from renal allograft recipients with biopsies showing Banff IA acute T-cell-mediated rejection. "Biopsy No ACR"=155 urine specimens from renal allograft recipients without ACR in biopsies. B. "Biopsy ACR"=43 urine specimens from renal allograft recipients with biopsies showing Banff IA acute T-cell-mediated rejection. "Stable"=2033 urine specimens from renal allograft recipients without ACR. In A & B mRNA levels are 18S rRNA normalized and log transformed. Plotted is mean value plus and minus standard error. P value calculated using Mann-Whitney Test.
Figure 1:
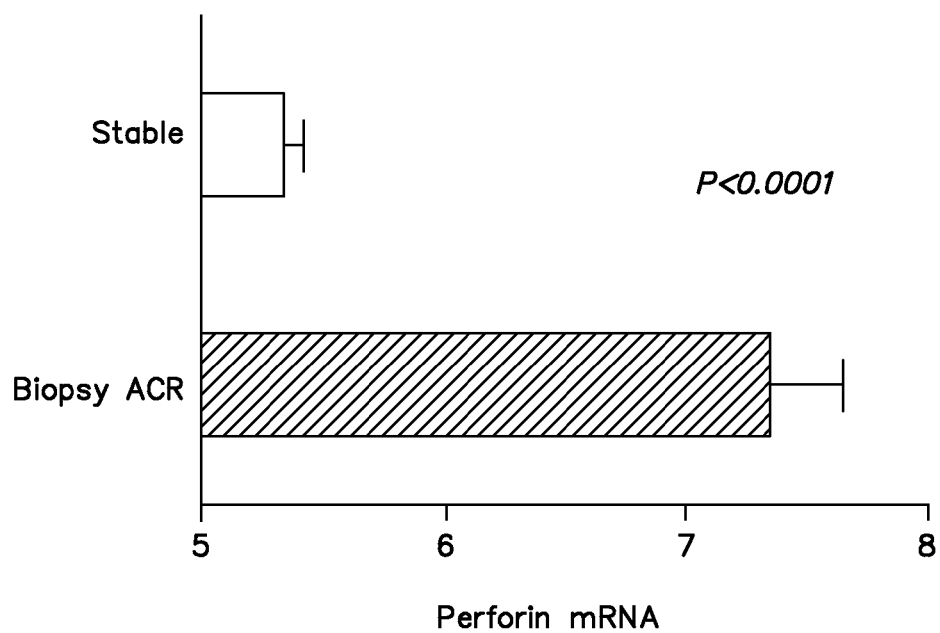
Figure 2:
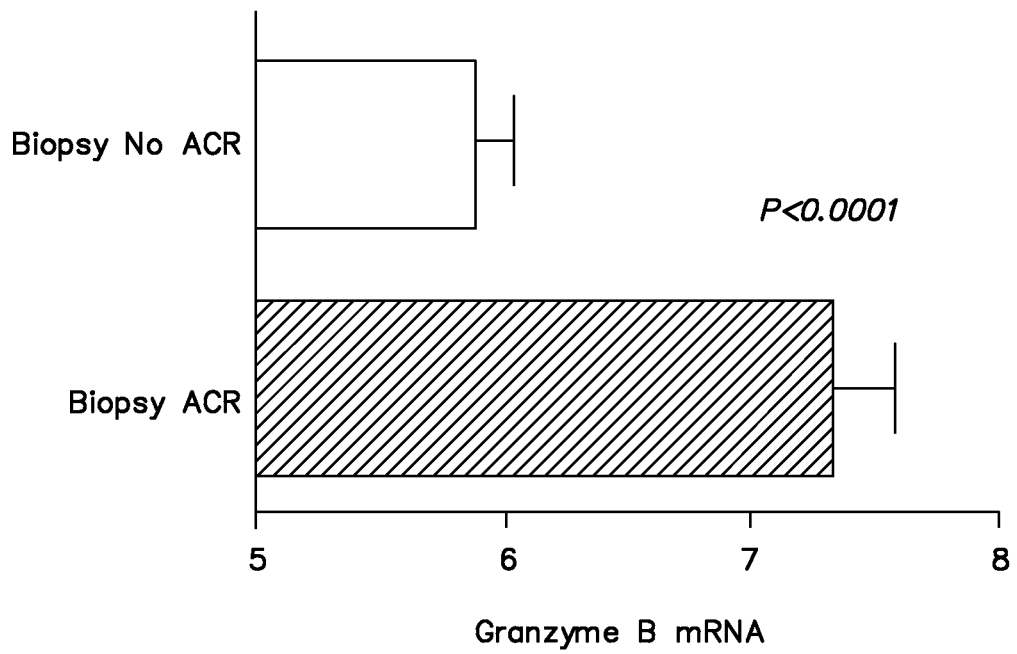
FIG. 2. Urinary Cell Granzyme B mRNA Levels are Diagnostic of Acute Cellular Rejection. A. "Biopsy ACR"=43 urine specimens from renal allograft recipients with biopsies showing Banff IA acute T-cell-mediated rejection. "Biopsy No ACR"=155 urine specimens from renal allograft recipients without ACR in biopsies. B. "Biopsy ACR"=43 urine specimens from renal allograft recipients with biopsies showing Banff IA acute T-cell-mediated rejection. "Stable"=2033 urine specimens from renal allograft recipients without ACR. In A&B mRNA levels are 18S rRNA normalized and log transformed. Plotted is mean value plus and minus standard error. P value calculated using Mann-Whitney Test.
Figure 2:
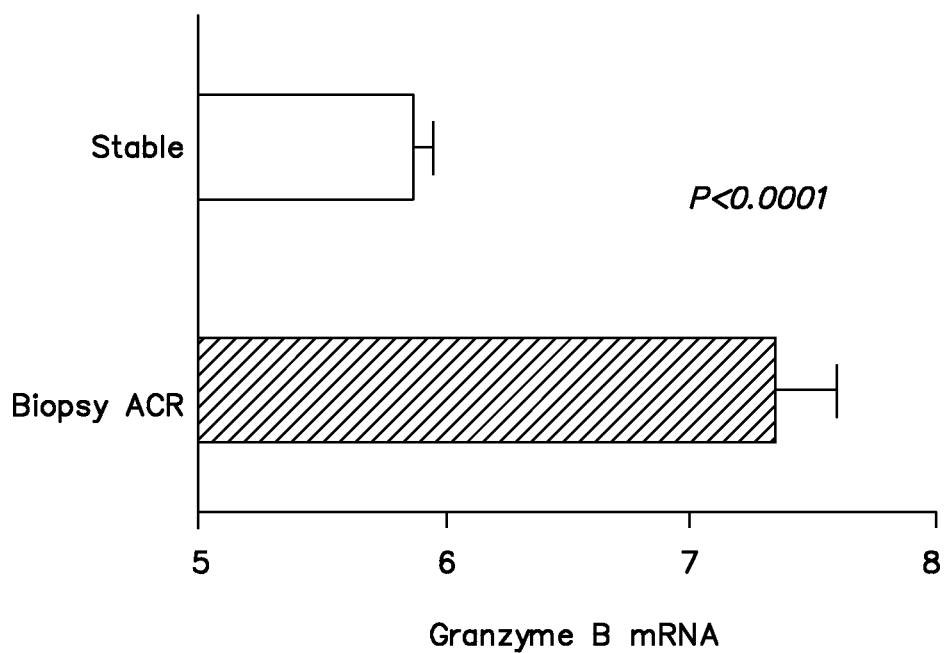
Figure 3:
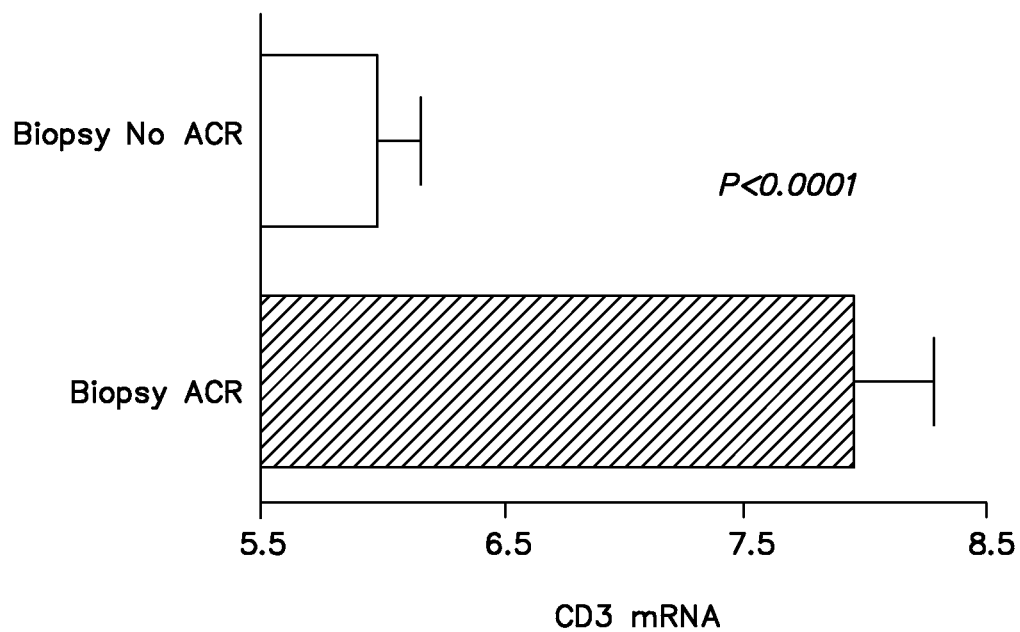
FIG. 3. Urinary Cell CD3 mRNA Levels are Diagnostic of Acute Cellular Rejection. A. "Biopsy ACR"=43 urine specimens from renal allograft recipients with biopsies showing Banff IA acute T-cell-mediated rejection. "Biopsy No ACR"=155 urine specimens from renal allograft recipients without ACR in biopsies. B. "Biopsy ACR"=43 urine specimens from renal allograft recipients with biopsies showing Banff IA acute T-cell-mediated rejection. "Stable"=2033 urine specimens from renal allograft recipients without ACR. In A& B mRNA levels 18S rRNA normalized and log transformed. Plotted is mean value plus and minus standard error. P value calculated using Mann-Whitney Test.
Figure 3:
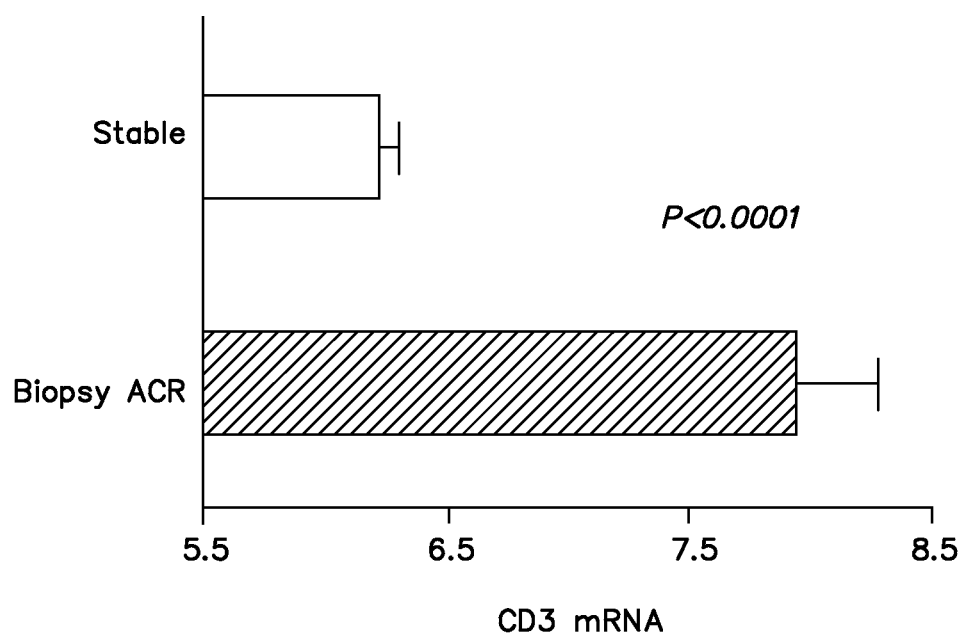
Figure 4:
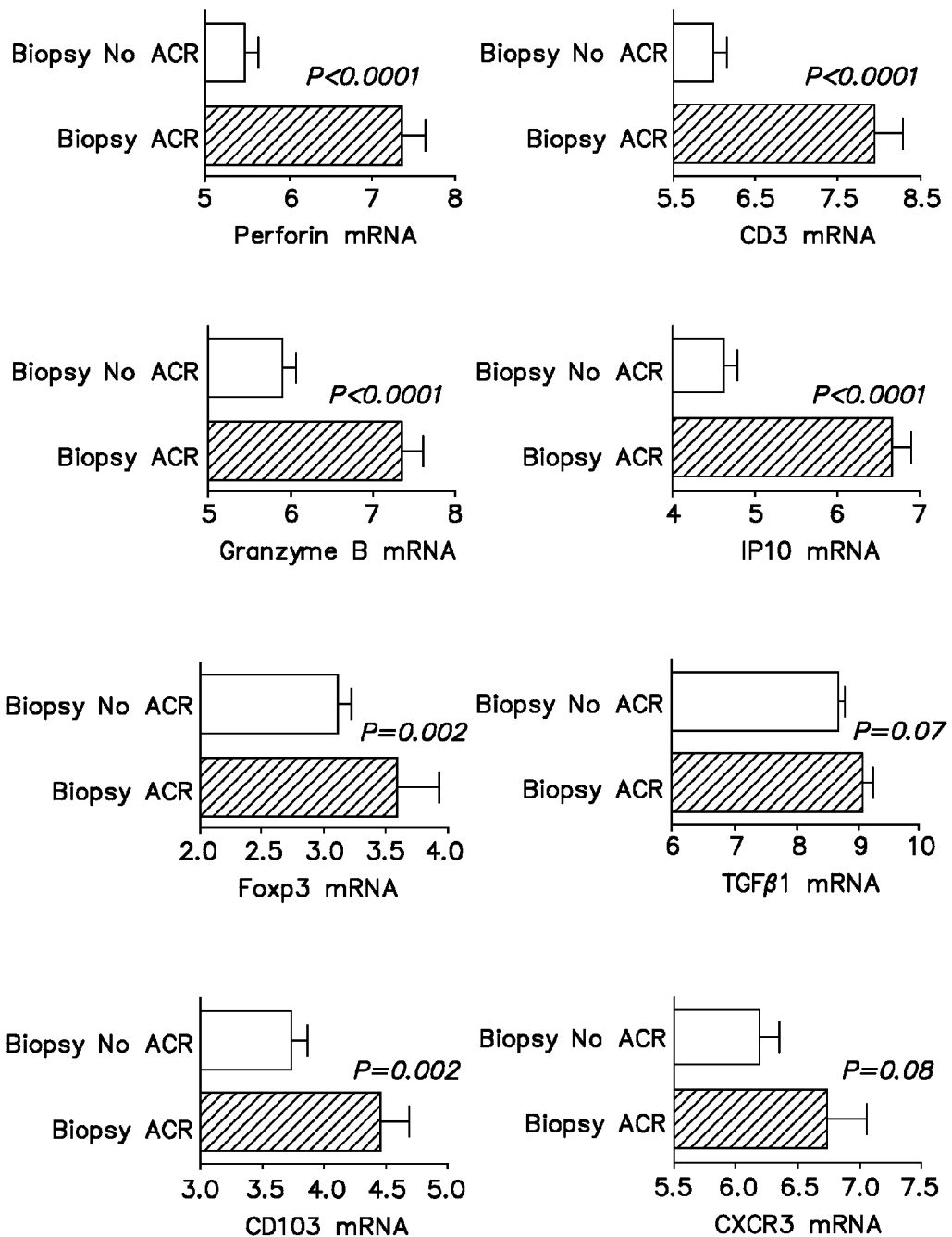
FIG. 4. Urinary Cell Levels of mRNA for Perforin, Granzyme B, CD3, IP-10, FoxP3, CD103, TGF-beta-1 and CXCR3. "Biopsy ACR"=43 urine specimens from renal allograft recipients with biopsies showing Banff IA acute T-cell-mediated rejection. "Biopsy No ACR"=155 urine specimens from renal allograft recipients without ACR in biopsies. mRNA levels 18S rRNA normalized and log transformed. Plotted is mean value plus and minus standard error. P value calculated using Mann-Whitney Test.
Figure 5:
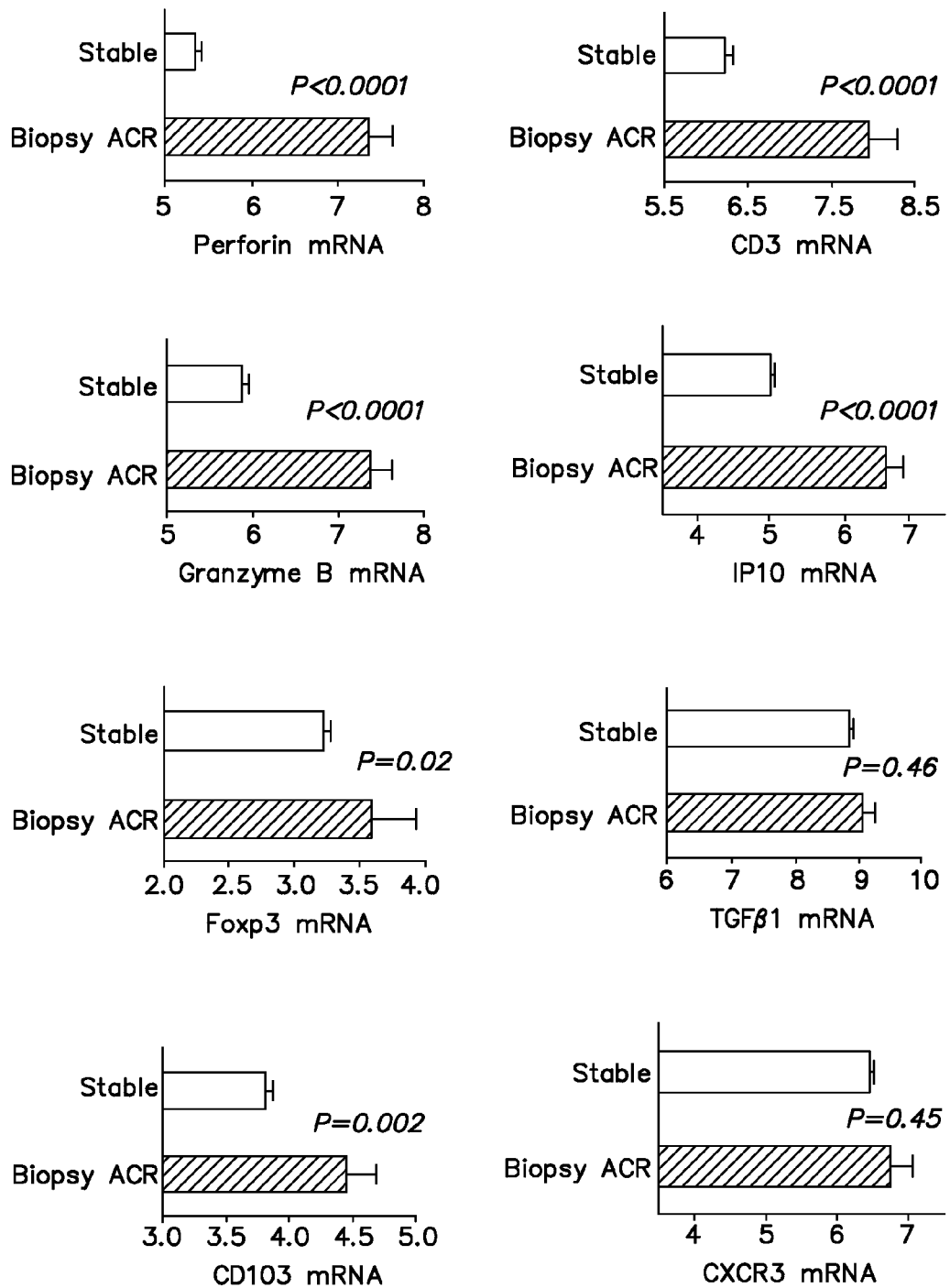
FIG. 5. Urinary Cell Levels of mRNA for Perforin, Granzyme B, CD3, IP-10, FoxP3, CD103, TGF-beta-1 and CXCR3. "Biopsy ACR"=43 urine specimens from renal allograft recipients with biopsies showing Banff IA acute T-cell-mediated rejection. "Stable"=2033 urine specimens from renal allograft recipients without ACR. mRNA levels 18S rRNA normalized and log transformed. Plotted is mean value plus and minus standard error. P value calculated using Mann-Whitney Test.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Definitions

An "anti-rejection agent" is any substance administered to a subject for the purpose of preventing or ameliorating a rejection state. Anti-rejection agents include, but are not limited to, azathioprine, cyclosporine, FK506, tacrolimus, mycophenolate mofetil, anti-CD25 antibody, antithymocyte globulin, rapamycin, ACE inhibitors, perillyl alcohol, anti-CTLA4 antibody, anti-CD40L antibody, anti-thrombin III, tissue plasminogen activator, antioxidants, anti-CD154, anti-CD3 antibody, thymoglobin, OKT3, corticosteroid, or a combination thereof. "Baseline therapeutic regimen" is understood to include those anti-rejection agents being administered at a baseline time, subsequent to the transplant. The baseline therapeutic regimen may be modified by the temporary or long-term addition of other anti-rejection agents, or by a temporary or long-term increase or decrease in the dose of one or all of the baseline anti-rejection agents.

The term "biopsy" refers to a specimen obtained by removing tissue from living patients for diagnostic examination. The term includes aspiration biopsies, brush biopsies, chorionic villus biopsies, endoscopic biopsies, excision biopsies, needle biopsies (specimens obtained by removal by aspiration through an appropriate needle or trocar that pierces the skin, or the external surface of an organ, and into the underlying tissue to be examined), open biopsies, punch biopsies (trephine), shave biopsies, sponge biopsies, and wedge biopsies. Biopsies also include a fine needle aspiration biopsy, a minicore needle biopsy, and/or a conventional percutaneous core needle biopsy.

A "sample" includes fluid samples obtained from a subject. A sample contains cells, proteins, nucleic acids or other cellular matter. A sample may also be the liquid phase of a body fluid from which sedimentary materials have been substantially removed. Exemplary samples include, but are not limited to, blood samples containing peripheral blood mononuclear cells (PBMCs), urine samples containing urinary cells, urine "supernatant" that is substantially free of cells, a sample of bronchoalveolar lavage fluid, a sample of bile, pleural fluid or peritoneal fluid, or any other fluid secreted or excreted by a normally or abnormally functioning allograft, or any other fluid resulting from exudation or transudation through an allograft or in anatomic proximity to an allograft, or any fluid in fluid communication with the allograft. A sample may also be obtained from essentially any body fluid including: blood (including peripheral blood), lymphatic fluid, sweat, peritoneal fluid, pleural fluid, bronchoalveolar lavage fluid, pericardial fluid, gastrointestinal juice, bile, urine, feces, tissue fluid or swelling fluid, joint fluid, cerebrospinal fluid, or any other named or unnamed fluid gathered from the anatomic area in proximity to the allograft or gathered from a fluid conduit in fluid communication with the allograft. A "post-transplantation sample" refers to a sample obtained from a subject after the transplantation has been performed.

"Baseline level of gene expression level" includes the particular gene expression level of a healthy subject or a subject with a well-functioning transplant. The baseline level of gene expression includes the gene expression level of a subject without acute rejection. The baseline level of gene expression can be a number on paper or the baseline level of gene expression from a control sample of a healthy subject or a subject with a well-functioning transplant.

The term "diagnosis" is used herein to refer to the identification or classification of a molecular or pathological state, disease or condition. For example, "diagnosis" may refer to identification of a particular type of acute rejection, e.g., acute cellular rejection.

The term "aiding diagnosis" is used herein to refer to methods that assist in making a clinical determination regarding the presence, degree or other nature, of a particular type of symptom or condition of acute rejection.

The term "prediction" is used herein to refer to the likelihood that a patient will develop acute rejection. Thus, prediction also includes the time period without acute rejection.

A "probe or primer" as used herein refers to a group of nucleic acids that may be used to detect one or more genes (perforin, granzyme B, IP-10, CD3, FoxP3, CXCR3, CD103, TGF-β1, PI-9, or TGF-β1). Detection may be, for example, through amplification as in PCR and RT-PCR, or through hybridization, or through selective destruction and protection, as in assays based on the selective enzymatic degradation of single or double stranded nucleic acids, or by detecting mRNA. Probes and/or primers may be labeled with one or more fluorescent, radioactive, quenchers, or other detectable moieties (including enzymes). Probes may be any size so long as the probe is sufficiently large to selectively detect the desired gene or be amplified.

Primers can be polynucleotides or oligonucleotides capable of being extended in a primer extension reaction at their 3' end. In order for an oligonucleotide to serve as a primer, it typically needs only be sufficiently complementary in sequence to be capable of forming a double-stranded structure with the template, or target, under the conditions employed. Establishing such conditions typically involves selection of solvent and salt concentration, incubation temperatures, incubation times, assay reagents and stabilization factors known to those in the art. The term primer or primer oligonucleotide refers to an oligonucleotide as defined herein, which is capable of acting as a point of initiation of synthesis when employed under conditions in which synthesis of a primer extension product that is complementary to a nucleic acid strand is induced, as, for example, in a DNA replication reaction such as a PCR reaction. Like non-primer oligonucleotides, primer oligonucleotides may be labeled according to any technique known in the art, such as with radioactive atoms, fluorescent labels, enzymatic labels, proteins, haptens, antibodies, sequence tags, mass label or the like. Such labels may be employed by associating them, for example, with the 5' terminus of a primer by a plurality of techniques known in the art. Such labels may also act as capture moieties. A probe or primer may be in solution, as would be typical for multiplex PCR, or a probe or primer may be adhered to a solid surface, as in an array or microarray. It is well known that compounds such as PNAs may be used instead of nucleic acids to hybridize to genes. In addition, probes may contain rare or unnatural nucleic acids such as inosine.

As used herein, the term polynucleotide includes nucleotide polymers of any number. The term polynucleotide includes a molecule comprising any number of nucleotides, preferably, less than about 200 nucleotides. More preferably, polynucleotides are between 5 and 100 nucleotides in length. Most preferably, polynucleotides are 15 to 100 nucleotides in length. The exact length of a particular polynucleotide, however, will depend on many factors, which in turn depend on its ultimate function or use. Some factors affecting the length of a polynucleotide are, for example, the sequence of the polynucleotide, the assay conditions in terms of such variables as salt concentrations and temperatures used during the assay, and whether or not the polynucleotide is modified at the 5' terminus to include additional bases for the purposes of modifying the mass:charge ratio of the polynucleotide, or providing a tag capture sequence which may be used to geographically separate a polynucleotide to a specific hybridization location on a DNA chip, for example.

As used herein, the term "transplantation" refers to the process of taking a cell, tissue, or organ, called a "transplant" or "graft" from one individual and placing it or them into a (usually) different individual. The individual who provides the transplant is called the "donor" and the individual who received the transplant is called the "host" (or "recipient"). An organ, or graft, transplanted between two genetically different individuals of the same species is called an "allograft". A graft transplanted between individuals of different species is called a "xenograft".

As used herein, "transplant rejection" refers to a functional and structural deterioration of the organ due to an active immune response expressed by the recipient, and independent of non-immunologic causes of organ dysfunction. Acute transplant rejection can result from the activation of recipient's T cells and/or B cells; the rejection primarily due to T cells is classified as T cell mediated acute rejection or acute cellular rejection (ACR) and the rejection in which B cells are primarily responsible is classified as antibody mediated acute rejection (AMR). In some embodiments, the methods and compositions provided can detect and/or predict acute cellular rejection.

As used herein, "subject" means a mammal. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; or the like. The term "subject" does not denote a particular age or sex. Preferably the subject is a human patient. In some embodiments, the subject is a human having received an organ transplant.

The term "up-regulation" or "up-regulated" are used interchangeably herein and refer to the increase or elevation in the amount of a target gene or a target protein. The term "up-regulation" or "up-regulated" also refers to the increase or elevation of processes or signal transduction cascades involving a target gene or a target protein. In some embodiments, upregulation includes increases above a baseline level of 10%, 15%, 20%, 25%, 30%, 35%, 40%, 45%, 50%, 55%, 60%, 65%, 70%, 75%, 80%, 85%, 90%, 95%, 100% or higher.

The term "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". The stringency of a hybridization reaction includes the difficulty with which any two nucleic acid molecules will hybridize to one another. Under stringent conditions, nucleic acid molecules at least 60%, 65%, 70%, 75% identical to each other remain hybridized to each other, whereas molecules with low percent identity cannot remain hybridized. A preferred, non-limiting example of highly stringent hybridization conditions are hybridization in 6.times.sodium chloride/sodium citrate (SSC) at about 45° C., followed by one or more washes in 0.2.times.SSC, 0.1% SDS at 50° C., preferably at 55° C., more preferably at 60° C., and even more preferably at 65.degree° C. When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to hydrogen bond with each other, according to generally accepted base-pairing rules.

A "gene" includes a polynucleotide containing at least one open reading frame that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art, some of which are described herein.

A "gene product" or "gene expression" includes an amino acid (e.g., peptide or polypeptide) generated when a gene is transcribed and translated. In some embodiments, the target gene expresses proteins of perforin, granzyme B, IP-10, CD3, FoxP3, CXCR3, CD103, TGF-β1, PI-9, or TGF-β1. The term "level of gene expression" as used herein refers to quantifying gene expression. In some embodiments, to accurately assess whether increased mRNA is significant, it is preferable to "normalize" gene expression to accurately compare levels of expression between samples, i.e., it is a baseline level against which gene expression is compared. Quantification of gene expression can be accomplished by methods known in the art, such as, for example, reverse transcription polymerase chain reaction (RT-PCR), TAQ-MAN® assays or the like. Gene expression can also be quantified by detecting the protein and/or peptide directly, in a variety of assay formats known to those of ordinary skill in the art, including but not limited to enzyme linked immunosorbent assay (ELISA), radioimmunoassay (RIA), immunofluorimetry, immunoprecipitation, equilibrium dialysis, immunodiffusion, immunoblotting, mass spectrometry and other techniques. See, e.g., Harlow and Lane, Antibodies: A Laboratory Manual, Cold Spring Harbor Laboratory, 1988; Weir, D. M., Handbook of Experimental Immunology, 1986, Blackwell Scientific, Boston.

As used herein, the term "biomarker" includes a polynucleotide or polypeptide molecule which is present or increased in quantity or activity in subjects having acute rejection or where the acute rejection is anticipated.

As used herein, the term "panel of biomarkers" includes a group of markers, the quantity or activity of each member of which is correlated with subjects having acute rejection or where the acute rejection is anticipated. In certain embodiments, a panel of markers may include only those markers which are either increased in quantity or activity in those subjects. In some embodiments, the panel of markers include one, two, three, four, five, six, seven, eight, or nine or more molecules (primers, probes, antibodies, etc.) that detect proteins of perforin, granzyme B, IP-10, CD3, FoxP3, CXCR3, CD103, PI-9, or TGF-β1.

General Background

The inventors have made the surprising discoveries that it is possible to anticipate the future development of acute cellular rejection with a high degree of accuracy; and diagnose acute cellular rejection with a high degree of sensitivity and specificity without performing a kidney transplant biopsy, by measuring the levels of expression of a small number of genes in cells in the urine samples from kidney transplant recipients. These discoveries are unanticipated since the immune response directed at the transplant is currently acknowledged to involve the participation of hundreds if not thousands of genes as exemplified by the use of techniques such as microarrays to measure levels of thousands of genes to investigate acute rejection.

In some embodiments, there are methods to detect existing and predict future acute rejection in a renal allograft comprising quantitatively determining the mRNA in cellular samples obtained from urine encoding the following proteins: perforin, granzyme B, proteinase inhibitor-9 (PI-9), interferon inducing protein-10 (IP-10), FoxP3, TGF-beta-1, CXCR3, or CD3. The amounts of most of these mRNAs are significantly higher in cells obtained from urine samples of patients undergoing acute rejection than in samples from patients not undergoing rejection. Surprisingly, weighted combinations of specific mRNAs from urine samples can identify acute rejection or predict its occurrence within a given time in the future. One embodiment of this invention describes a method of diagnosing acute cellular rejection by obtaining a signature weighted combination of the amounts of mRNA of perforin, IP-10, Fox p3 and TGF-beta1 in urine sample obtained from a transplant patient, with weights based on a logistic regression model.

Another embodiment of this invention describes a non-invasive method to anticipate the future development of acute cellular rejection of kidney transplants by measurement of messenger RNA (mRNA) in cells in urine samples from renal allograft recipients. A combination of levels of mRNAs for perforin, PI-9, IP-10, CXCR3, CD3 and granzyme B accurately distinguishes patients who will develop acute cellular rejection in the near future from those who will not develop acute cellular rejection. In particular, a weighted combination of mRNA levels of perforin and PI-9 in urine samples from transplant patients predict ACR in 60 to 90 days. Similarly, a weighted linear combination of perforin, 1P-10, CXCR3, and FoxP3 predict ACR in 30 to 59 days. Further, a weighted linear combination of perforin, PI-9, 1P-10, CXCR3, and CD3, are indicative of ACR in 15 to 29 days.

In some embodiments, the inventors show quantitative PCR assays and mRNA profiling protocols and have demonstrated that urinary cell levels of mRNA for perforin, granzyme B, Foxp3, CD3ε, CD103, PI-9, IP-10 and CXCR3 have been shown to be predictive of acute rejection of human renal allografts (1-8). These observations have been confirmed and extended by other investigators. It should be realized that none of these markers has been validated to an extent that it will allow the application in the management of kidney transplant recipients. Most studies have been single center without matched biopsies, and are potentially confounded by other co-existing conditions that may affect the expression of the selected marker. Very importantly, detailed studies that included sequential urine samples collected over the first 12 months of transplantation and using a large cohort of kidney transplant recipients have not been performed. These shortcomings have contributed to the current lack of the use urinary cell mRNA levels as surrogates of transplant biopsy or for anticipating future episodes acute rejection.

The existing shortcomings that prevented practical application of urinary cell mRNA levels for the clinical management of renal transplant recipients have been overcome by the current invention; in what is likely to be the largest study of urinary cell mRNA profiling of kidney transplant recipients (described in detail in subsequent sections), the inventors identified urinary cell mRNA profiles (urinary cell mRNA expression signatures) that are diagnostic of acute cellular rejection in kidney allografts as well as urinary cell mRNA profiles that are predictive of development of an episode of acute rejection of human renal transplants within a certain time in the future.

Detecting Acute Transplant Rejection

In one embodiment, there is a method of detecting a subject having received an organ transplant with acute rejection, the method comprising the steps of obtaining a biological sample from the subject; detecting an amount of at least one protein indicative of acute rejection in the sample, wherein the protein is one of perforin, granzyme B, IP-10, CD3, FoxP3, CXCR3, CD103 and/or TGF-β1; and comparing the amount of the protein in the sample to a control, wherein increases between the amount of the protein in the sample relative to the control indicates the subject has acute cellular rejection.

In another embodiment, there is a method for detecting acute transplant rejection of a transplanted organ in a patient, the method comprising determining a level of gene expression of perforin, granzyme B, IP-10, CD3, FoxP3, CXCR3, CD103 and/or TGF-β1 in a sample from the patient; and comparing the level of gene expression to a baseline level of gene expression of perforin, granzyme B, IP-10, CD3, FoxP3, CXCR3, CD103 and/or TGF-β1, wherein upregulation of gene expression of perforin, granzyme B, IP-10, CD3, FoxP3, CXCR3, CD103 and/or TGF-β1 in the sample from the patient relative to the baseline level of gene expression indicates acute rejection of the transplanted organ.

The invention is based, in part, on the observation that increased expression of many different genes and/or the encoded proteins comprising perforin, granzyme B, IP-10, CD3, FoxP3, CXCR3, CD103, TGF-β1, or PI-9 mentioned in Table 3 is associated with acute rejection and/or can be used to predict acute rejection in a transplant patient. As a result of the data described herein, compositions and methods are now available for the rapid and reliable detection of acute rejection or prediction of acute rejection, even without allograft biopsy.

The amounts of any combinations of these proteins perforin, granzyme B, IP-10, CD3, FoxP3, CXCR3, CD103, PI-9, or TGF-β1 may be detected according to the present application and compared to a control (baseline level). In one embodiment, a difference in the amount of only one protein can indicate that the subject has or is developing acute rejection. However, in alternate embodiments, changes in the amounts of any combination of two, three, four, six, eight, nine or more proteins can indicate that the subject has or is developing acute rejection. In this way, the dose of ant-rejection agents can be modified, e.g., increased or decreased or discontinued and/or new agents added to the treatment regimen. In some embodiments, other treatment modalities can be initiated, such as for example, plasmapheresis.

The proteins that can be upregulated include perforin and/or granzyme B. Perforin is a protein, stored and secreted from the granules of cytotoxic effector cells, forms pores in the target cell membrane, and causes cell death. Granzyme B, expressed primarily by activated cytotoxic cells, is a serine peptidase, and is an integral member of the lytic machinery of cytotoxic cells. In the granule exocytosis model of cytotoxicity, perform creates holes in the target cell membrane and facilitates the entry of granzyme B into the target cells. Granzymne B then induces DNA fragmentation and cell death via activation of proapoptotic caspase 3. The gene encoding granzyme B and perforin and their accession numbers and primers and labeled probes to identify them are mentioned in Table 3. In some embodiments, mRNA from a urine sample is detected and quantified for perforin and/or granzyme B.

The proteins that can be upregulated include IP-10, which is interferon-inducible protein-10. IP-10 is a member of the chemokine family of cytokines and is induced in a variety of cells in response to interferon gamma and lipopolysaccharide. IP-10 is a 10 kDa protein that in humans is encoded by the CXCL10 gene. The gene encoding IP-10 and its accession number and primers and labeled probes to identify it are mentioned in Table 3. In some embodiments, mRNA from a urine sample is detected and quantified for IP-10.

The proteins that can be upregulated include CD3. The CD3 antigen is present on mature human T cells, thymocytes and a subset of natural killer cells. It is associated with the T cell receptor (TCR) and is responsible for the signal transduction of the TCR. Owing to its central role in modulating T cell activity, the TCR/CD3 complex has been the subject of much research aimed at developing molecules capable of binding TCR/CD3. Much of this work has focused on the development of antibodies specific for the human CD3 antigen. The gene encoding CD-3 and its accession number and primers and labeled probes to identify it are mentioned in Table 3. In some embodiments, mRNA from a urine sample is detected and quantified for CD-3.

The proteins that can be upregulated include FoxP3. FoxP3 is a member of the forkhead family of transcription factors. Foxp3 programs the development and function of CD4+CD25+ regulatory T cells, whereas ectopic expression of Foxp3 in conventional T cells confers suppressive activity. The gene encoding FoxP3 and its accession number and primers and labeled probes to identify it are mentioned in Table 3. In some embodiments, mRNA from a urine sample is detected and quantified for FoxP3.

The proteins that can be upregulated include CXCR3, which is a chemokine or chemotactic cytokines. The CXCR3 chemokine receptor is expressed primarily in T lymphocytes. The gene encoding CXCR3 and its accession number and primers and labeled probes to identify it are mentioned in Table 3. In some embodiments, mRNA from a urine sample is detected and quantified for CXCR3.

The proteins that can be upregulated include CD103 (Cluster of Differentiation 103). CD103 is in the integrin family and is a heterodimer that plays a diverse and redundant role in T-cell activation, homing, and delivery of effector function. The gene encoding CD103 and its accession number and primers and labeled probes to identify it are mentioned in Table 3. In some embodiments, mRNA from a urine sample is detected and quantified for CD103.

The proteins that can be upregulated include TGF-β1. Transforming growth factor beta-1 (TGF-β1) is a polypeptide member of the transforming growth factor beta superfamily of cytokines. It is a secreted protein that performs many cellular functions, including the control of cell growth, cell proliferation, cell differentiation and apoptosis. In humans, TGF-β1 is implicated in a variety of renal diseases. Almost every cell in the body has been shown to make some form of TGF-β1, and almost every cell has receptors for TGF-β1, the context of which determines their functionality. The TGF-β system is also a likely mediator of renal apoptosis. TGF-β is intimately connected with glomerular sclerosis, mesangial matrix expansion, and tubulointerstitial fibrosis in experimental rodent models and human glomerulnephritis. The gene encoding TGF-β1 and its accession number and primers and labeled probes to identify it are mentioned in Table 3. In some embodiments, mRNA from a urine sample is detected and quantified for TGF-β1.

The human intracellular serpin proteinase inhibitor (PI-9) is a protein able to inhibit the activity of granzyme B. PI-9 is present in CD4+ cells, CD8+ T cells, NK cells, and at lower levels in B cells and myeloid cells. The gene encoding PI-9 and its accession number and primers and labeled probes to identify it are mentioned in Table 3. In some embodiments, mRNA from a urine sample is detected and quantified for PI-9.

In certain aspects of the present application, the level of gene expression is determined for one or more genes in sample obtained from a subject. The sample can be a fluid sample such as a blood sample, preferably containing peripheral blood mononuclear cells (PBMCs), a urine sample, preferably containing urinary cells, a sample of bronchoalveolar lavage fluid, a sample of bile, pleural fluid or peritoneal fluid, or any other fluid secreted or excreted by a normally or abnormally functioning allograft, or any other fluid resulting from exudation or transudation through an allograft or in anatomic proximity to an allograft, or any fluid in fluid communication with the allograft.

Any method known to those in the art can be employed for determining the level of gene expression. For example, a microarray can be used. Microarrays are known in the art and consist of a surface to which probes that correspond in sequence to gene products (e.g. mRNAs, polypeptides, fragments thereof etc.). can be specifically hybridized or bound to a known position. Hybridization intensity data detected by the scanner are automatically acquired and processed by the Affymetrix Microarray Suite (MAS5) software. Raw data is normalized to expression levels using a target intensity of 150. An alternate and preferred method to measure gene expression profiles of a small number of different genes is by e.g. either classical TaqMan® Gene Expression Assays or TaqMan® Low Density Array—micro fluidic cards (Applied Biosystems). Here, quantitative data are obtained by real-time RT-PCR in a small reaction volume.

The transcriptional state of a cell may be measured by other gene expression technologies known in the art. Several such technologies produce pools of restriction fragments of limited complexity for electrophoretic analysis, such as methods combining double restriction enzyme digestion with phasing primers (e.g. EP-A1-0 534858), or methods selecting restriction fragments with sites closest to a defined mRNA end (e.g. Prashar et al; Proc. Nat. Acad. Sci., 93, 659-663, 1996). Other methods statistically sample cDNA pools, such as by sequencing sufficient bases (e.g. 20-50 bases) in each multiple cDNAs to identify each cDNA, or by sequencing short tags (e.g. 9-10 bases) which are generated at known positions relative to a defined mRNA end (e.g. Velculescu, Science, 270, 484-487, 1995) pathway pattern.

In one embodiment, the mRNA of perforin, granzyme B, IP-10, CD3, FoxP3, CXCR3, CD103, PI-9, or TGF-β1 is detected from a cell sample from the recipient of an organ transplant. Any method known to those in the art can be employed for determining the level of mRNA of perforin, granzyme B, IP-10, CD3, FoxP3, CXCR3, CD103, PI-9, or TGF-β1. Typically, total RNA, which includes mRNA, is isolated. RNA can be isolated from the sample by any method known to those in the art. For example, commercial kits, such as the TRI Reagent® commercially available from Molecular Research Center, Inc. (Cincinnati, Ohio), can be used to isolate RNA.

The quantification of mRNA of perforin, granzyme B, IP-10, CD3, FoxP3, CXCR3, CD103, PI-9, or TGF-β1 from total mRNA from the sample can be performed by any method known to those in the art. For example, kinetic, quantitative PCR involves reverse transcribing mRNA of perforin, granzyme B, IP-10, CD3, FoxP3, CXCR3, CD103, PI-9, or TGF-β1 by using reverse-transcriptase polymerase chain reaction (RT-PCR) to obtain perforin, granzyme B, IP-10, CD3, FoxP3, CXCR3, CD103, PI-9, or TGF-β1 cDNA. The cDNA can then, for example, be amplified by PCR followed by quantitation using a suitable detection apparatus. See Example 2 below for a description of the quantitation of mRNA of perforin, granzyme B, IP-10, CD3, FoxP3, CXCR3, CD103, PI-9, or TGF-β1 by kinetic, quantitative PCR.

Generally, the isolated mRNA of perforin, granzyme B, IP-10, CD3, FoxP3, CXCR3, CD103, PI-9, or TGF-β1 may be amplified by methods known in the art. Amplification systems utilizing, for example, PCR or RT-PCR methodologies are known to those skilled in the art. For a general overview of amplification technology, see, for example, Dieffenbach et al., PCR Primer: A Laboratory Manual, Cold Spring Harbor Laboratory Press, New York (1995). For example, levels of mRNA of perforin, granzyme B, IP-10, CD3, FoxP3, CXCR3, CD103, TGF-131, PI-9, or TGF-β1 can be determined using kinetic, quantitative PCR.

An alternative method for determining the level of mRNA of perforin, granzyme B, IP-10, CD3, FoxP3, CXCR3, CD103, PI-9, or TGF-β1 includes the use of molecular beacons and other labeled probes useful in, for example multiplex PCR. In a multiplex PCR assay, the PCR mixture contains primers and probes directed to the perforin, granzyme B, IP-10, CD3, FoxP3, CXCR3, CD103, PI-9, or TGF-β1 PCR product. Typically, a single fluorochrome is used in the assay. The molecular beacon or probe is detected to determine the level of mRNA of perforin, granzyme B, IP-10, CD3, FoxP3, CXCR3, CD103, PI-9, or TGF-β1. Molecular beacons are described, for example, by Tyagi and Kramer (Nature Biotechnology 14, 303-308, 1996) and by Andrus and Nichols in U.S. Patent Application Publication No. 20040053284.

Another method includes, for instance, quantifying cDNA (obtained by reverse transcribing the mRNA of perforin, granzyme B, IP-10, CD3, FoxP3, CXCR3, CD103, PI-9, or TGF-β1 using a fluorescence based real-time detection method, such as the ABI PRISM 7500, 7700, or 7900 Sequence Detection System (TaqMan®) commercially available from Applied Biosystems, Foster City, Calif. or similar system as described by Heid et al., (Genome Res. 1996; 6:986-994) and Gibson et al. (Genome Res. 1996; 6:995-1001).

Generally, the level of perforin, granzyme B, IP-10, CD3, FoxP3, CXCR3, CD103, PI-9, or TGF-β1 in a cell sample is upregulated if the gene expression of perforin, granzyme B, IP-10, CD3, FoxP3, CXCR3, CD103, PI-9, or TGF-β1 is increased. For example, increase or elevation of processes or signal transduction cascades involving perforin, granzyme B, IP-10, CD3, FoxP3, CXCR3, CD103, PI-9, or TGF-β1. In some embodiments, upregulation includes increases above a baseline level of 10%, 15%, 20%, 25%, 30%, 35%, 40%, 45%, 50%, 55%, 60%, 65%, 70%, 75%, 80%, 85%, 90%, 95%, 100% or higher.

For example, a discriminatory level for upregulated gene expression (e.g., the baseline magnitude of gene expression) of perforin, granzyme B, IP-10, CD3, FoxP3, CXCR3, CD103, PI-9, or TGF-β1 includes the mean±95% confidence interval of a group of values observed in nonrejecting transplants (e.g., baseline levels or control levels). Upregulation of gene expression of perforin, granzyme B, IP-10, CD3, FoxP3, CXCR3, CD103, PI-9, or TGF-β1 is considered to be significantly greater if the value is greater than the mean±95% confidence interval of a group of values observed in nonrejecting transplants. Similarly, the level of perforin, granzyme B, IP-10, CD3, FoxP3, CXCR3, CD103, PI-9, or TGF-β1 in the cell sample is considered to be significantly lower if the perforin, granzyme B, IP-10, CD3, FoxP3, CXCR3, CD103, PI-9, or TGF-β1 value is lower than the mean±95% confidence interval of a group of values observed in nonrejecting transplants.

In some embodiments, the level of gene expression is determined using log-transformed mRNA levels of perforin, granzyme B, IP-10, PI-9, CD3, FoxP3, CXCR3, CD103 and/or TGF-β1 in a urine cell sample from the patient. The log transformation or mRNA levels substantially reduced the positive skew in the data. In some embodiments, the level of gene expression is determined using log-transformed mRNA levels determined by normalizing mRNA levels to 18S rRNA using a logistic regression model of perforin, granzyme B, IP-10, CD3, FoxP3, CXCR3, CD103 and/or TGF-β1 or a weighted combination of log transformed, normalized mRNA levels of perforin, IP-10, Foxp3 and TGF-β1 based on a logistic regression model. Logistic regression models are used for prediction of the probability of occurrence of acute rejection by fitting data to a logistic curve. It is a generalized linear model used for binomial regression.

In some embodiments, for interpretation of quantitative gene expression measurements, a normalizer may be needed to correct expression data for differences in cellular input, RNA quality, and RT efficiency between samples. In some embodiments, to accurately assess whether increased mRNA is significant, the gene expression can be normalized to accurately compare levels of expression between samples, e.g., it is a baseline level against which gene expression is compared. In quantitative assays, such as for example, quantitative real-time Reverse Transcriptase-PCR (RT-PCR) normalization can be performed using housekeeping genes as references against the expression level of a gene under investigation. Normalization includes rendering the measurements of different arrays or PCR or in particular RT-PCR experiments comparable by reducing or removing the technical variability. Within these experiments there exists a multiplicity of sources capable of falsifying the measurements. Possible technical sources of interference are: different efficiency in reverse transcription, labeling or hybridization reactions, as well as problems with the arrays, batch effects in reagents, or lab-specific conditions. By normalization a more robust detection of gene expression can occur.

Typically, normalization involves use of a "housekeeping gene" which is utilized as a reference, internal control or reference values in the quantification of gene expression. The housekeeping gene allows an identification and quantitative analysis of a gene whose activity is regulated differentially in different pathological conditions. A house keeping gene exhibits minimum change of expression and transcription across different RNA samples and thus serves as a control, or reference, for the measurement of variable gene activities across different samples. House keeping genes for mRNA detection include, for example, β2-Microglobulin (β2M), Glucose-6-phosphate dehydrogenase (G6PDH), 5-aminolevulinate synthase (ALAS or ALAS 1) Hypoxanthinephophoribosyltransferase (HPRT), Porphobilinogen deaminase (PBGD), 18S rRNA, or the like. In some embodiments, 18S rRNA is used for normalization in gene expression analysis. Various house keeping genes and normalization reagents are available from many sources including Applied Biosystems, (Foster City, Calif.), and geNorm® kits Hoffmann-La Roche (Nutley, N.J.).

In some embodiments, the level of 18S-normalized mRNA for perforin, granzyme B, IP-10, CD3, FoxP3, CXCR3, CD103, PI-9, or TGF-β1 can deviate from a normal distribution (P<0.001) and the natural log-transformation substantially reduces this deviation. Statistical calculations can be performed using, for example, GraphPad Prism software version 4.0 (GraphPad Software, Inc. La Jolla, Calif.). By using 18S-normalized levels, the Mann-Whitney U test to test the difference between the group with acute rejection and the group with normal biopsy results can be obtained. Categorical variables can be compared using, for example, Fisher's exact test or chi-square analysis.

Receiver Operating Characteristic (ROC) curves can be generated for individual mRNA levels and a linear combination of mRNA levels to determine the cutoff points that yielded the highest combined sensitivity and specificity for detecting ACR or anticipating ACR. This involves measuring the mRNA levels that encode the proteins: perforin, granzyme B, IP-10, CD3, FoxP3, CXCR3, CD103, PI-9, or TGF-β1 alone or in any combination. For example, all nine markers can be measured alone, all together, or in any combination, such as for example, mRNA levels of perforin can be measured with one or more of granzyme B, with IP-10, CD3, FoxP3, CXCR3, CD103, PI-9, or TGF-β1; or mRNA levels of granzyme B can be measured with one or more of perforin, IP-10, CD3, FoxP3, CXCR3, CD103, PI-9, or TGF-β1; or mRNA levels of IP-10 can be measured with one or more of perforin, granzyme B, CD3, FoxP3, CXCR3, CD103, PI-9, or TGF-β1; or mRNA levels of CD3 can be measured with one or more of perforin, granzyme B, IP-10, FoxP3, CXCR3, CD103, PI-9, or TGF-β1; or mRNA levels of FoxP3 can be measured with one or more of perforin, granzyme B, IP-10, CD3, CXCR3, CD103, PI-9, or TGF-β1; or mRNA levels of CXCR3 can be measured with one or more of perforin, granzyme B, IP-10, FoxP3, CD103, CD3, PI-9, or TGF-β1; or mRNA levels of CD103 can be measured with one or more of perforin, granzyme B, IP-10, FoxP3, CXCR3, CD3, PI-9, or TGF-β1; or mRNA levels of PI-9 can be measured with one or more of perforin, granzyme B, IP-10, FoxP3, CXCR3, CD3, CD103, or TGF-β1; or mRNA levels of TGF-β1 can be measured with one or more of perform, granzyme B, IP-10, FoxP3, CXCR3, CD103, CD-3, or PI-9 to detect acute rejection or anticipate rejection. These combinations are then weighted based on increased expression. These statistical analyses with different biomarkers are described in Afaneh C, Muthukumar T, Lubetzky M, Ding R, Snopkowski C, Sharma V K, Seshan S, Dadhania D, Schwartz J E, Suthanthiran M. Urinary Cell Levels of mRNA for OX40, OX40L, PD-1, PD-L1, or PD-L2 and Acute Rejection of Human Renal Allografts. Transplantation. 2010 Nov. 12, and Zhang et al., A Linear Regression Framework For Receiver Operating Characteristics (ROC) Curve Analysis University of Washington Biostatistics Working Paper Series (2005). The references are hereby incorporated by reference into the present application. Other statistical analysis methods for quantifying biomarkers known in the art can be used as well.

In some embodiments, the mRNA levels of perforin, granzyme B, IP-10, PI-9, CD3, FoxP3, CXCR3, CD103 and/or TGF-β1 are compared to a base line level or a control level observed in nonrejecting organs and may include the level of perforin, granzyme B, IP-10, PI-9, CD3, FoxP3, CXCR3, CD103 and/or TGF-β1 of the same patient before the organ transplant; the average level of perforin, granzyme B, IP-10, PI-9, CD3, FoxP3, CXCR3, CD103 and/or TGF-β1 in patients of similar age, gender, race, graft-donor source, Banff histologic grade, or initial anti-rejection treatment as the patient, and/or a value for the level of perforin, granzyme B, IP-10, PI-9, CD3, FoxP3, CXCR3, CD103 and/or TGF-β1 accepted in the art.

A baseline or control sample is typically the level of perforin, granzyme B, IP-10, PI-9, CD3, FoxP3, CXCR3, CD103 and/or TGF-β1 from a healthy person or a person with a well-functioning (e.g., stable) transplanted organ. A well-functioning (e.g., stable) transplanted organ may be defined as a transplanted organ without acute rejection, and preferably a transplanted organ that has not developed transplant dysfunction or morphologic evidence of transplant injury in areas of the transplant. For example, a stable functioning kidney transplant may be defined as having a serum creatinine concentration that has not changed by more than approximately 0.2 mg per deciliter during the seven days before and the seven days after collection of the biologic specimen for perforin, granzyme B, IP-10, PI-9, CD3, FoxP3, CXCR3, CD103 and/or TGF-β1 measurements.

It will be understood by those of ordinary skill in the art that it is not necessary to determine the level of perforin, granzyme B, IP-10, PI-9, CD3, FoxP3, CXCR3, CD103 and/or TGF-β1 mRNA or perforin, granzyme B, IP-10, PI-9, CD3, FoxP3, CXCR3, CD103 and/or TGF-β1 protein in a baseline or control sample every time the method is conducted. For example, the perforin, granzyme B, IP-10, PI-9, CD3, FoxP3, CXCR3, CD103 and/or TGF-β1 levels in the cell sample from the transplanted organ or in the cell sample from the peripheral blood can be compared to that of one or more previously determined control samples or to a level recognized by the physician or clinician conducting the method of a consensus of medical and/or clinical practitioners.

In some embodiments, there is provided a method for detecting acute rejection where levels of gene expression are compared to a baseline level of gene expression, which is performed using log-transformed mRNA levels in the urine cell sample and comparing it with log-transformed mRNA levels of perforin, granzyme B, IP-10, CD3, FoxP3, CXCR3, CD103 and/or TGF-β1 of a baseline sample from a subject without acute rejection of a transplanted organ. If there is upregulation of mRNA levels of perforin, granzyme B, IP-10, CD3, FoxP3, CXCR3, CD103 and/or TGF-β1 from the urine cell sample relative to the baseline level of gene expression in the baseline sample, this indicates acute rejection of the transplanted organ. If this is the case, then further steps such as determining the patient's serum creatinine level in peripheral blood, administering treatment comprising plasmapheresis to the patient and any anti-rejection therapy can be modified (e.g., dose increased, decreased, additional agents added or agents discontinued, etc.).

Proteins

In some embodiments, the perforin, granzyme B, IP-10, CD3, FoxP3, CXCR3, CD103, PI-9, or TGF-β1 proteins expressed can be measured directly. Increased levels of certain proteins can be used to detect acute rejection and may also provide diagnostic information about transplants. In certain embodiments, one or more proteins encoded by genes of any of the genes listed in Table 3 may be detected, and elevated or decreased protein levels may be used to diagnose acute graft rejection or anticipate acute graft rejection.

In some embodiments, protein levels are detected in a post-transplant fluid sample, and in a particularly preferred embodiment, the fluid sample is urine. In view of this specification, methods for detecting proteins are well known in the art. Examples of such methods include Western blotting, enzyme-linked immunosorbent assays (ELISAs), one- and two-dimensional electrophoresis, mass spectroscopy and detection of enzymatic activity. Suitable antibodies may include polyclonal, monoclonal, fragments (such as Fab fragments), single chain antibodies and other forms of specific binding molecules. Briefly, these protein detection assays are normally based on incubating an antibody specific to the protein with a sample suspected of containing the protein, and detecting the presence of a complex between the antibody and the protein.

Predicting Acute Transplant Rejection

In one embodiment, there is a method of predicting acute rejection, the method comprising the steps of obtaining a biological sample from the subject; detecting an amount of at least one protein indicative of acute rejection in the sample, wherein the protein is one of perform, granzyme B, IP-10, CD3, FoxP3, CXCR3, CD103, and/or PI-9 and/or TGF-β1; and comparing the amount of the protein in the sample to a control, wherein increases between the amount of the protein in the sample relative to the control indicates that the subject will have acute cellular rejection. In this embodiment, the panel of markers include one, two, three, four, five, six, seven, eight, or nine proteins or molecules that detect proteins of perforin, granzyme B, IP-10, CD3, FoxP3, CXCR3, CD103, TGF-β1, PI-9, or TGF-β1. One marker, PI-9, in some embodiments, is particularly relevant to predict acute rejection.

Any method known to those in the art, as discussed above, can be employed for determining the level of gene expression. Microarrays, TaqMan® Gene Expression Assays (Applied Biosystems), molecular beacons, scorpions, SYBR Green, RT-PCR, or the like. Here, in the Example Section, quantitative data are obtained by real-time RT-PCR in a small reaction volume.

In some embodiments, there is a method for predicting acute rejection of a transplanted organ in a patient, the method comprising determining a level of gene expression of perforin, granzyme B, IP-10, CD103, PI-9, CXCR3, CD3 and/or FoxP3 in a sample from the patient; and comparing the level of gene expression to a baseline level of gene expression of perforin, granzyme B, IP-10, CD103, PI-9, CXCR3, CD3 and/or FoxP3, wherein upregulation of gene expression of perforin, granzyme B, IP-10, CD103, PI-9, CXCR3, CD3 and/or FoxP3 in the sample relative to the baseline level of gene expression predicts acute rejection of the transplanted organ.

In some embodiments, upregulation includes increases above a baseline level of 10%, 15%, 20%, 25%, 30%, 35%, 40%, 45%, 50%, 55%, 60%, 65%, 70%, 75%, 80%, 85%, 90%, 95%, 100% or higher.

In some embodiments, the method of determining gene expression to predict acute rejection includes using log-transformed mRNA levels of perforin, granzyme B, IP-10, CD103, PI-9, CXCR3, CD3 and/or FoxP3 in a urine cell sample from the patient and the acute transplant rejection comprises acute cellular rejection. In some embodiments, the method for predicting acute rejection includes normalizing mRNA levels to 18S rRNA using a logistic regression model of perform, granzyme B, IP-10, CD103, PI-9, CXCR3, CD3 and/or FoxP3 or using a weighted combination of log transformed, normalized mRNA levels of perform, granzyme B, IP-10, CD103, PI-9, CXCR3, CD3 and/or FoxP3 based on a logistic regression model.

In some embodiments, the method for predicting acute rejection involves comparing the levels of gene expression to a baseline level of gene expression by using log-transformed mRNA levels in the urine cell sample and comparing it with log-transformed mRNA levels of perforin, granzyme B, IP-10, CD103, PI-9, CXCR3, CD3 and/or FoxP3 of a baseline sample from a subject without acute rejection of a transplanted organ, where upregulation of mRNA levels of perforin, granzyme B, IP-10, CD103, PI-9, CXCR3, CD3 and/or FoxP3 from the urine cell sample relative to the baseline level of gene expression in the baseline sample predicts acute rejection of the transplanted organ.

The number of days prior to acute rejection is shown in Table 2. These include 90 to 60 days before acute rejection is confirmed by biopsy, or 59 to 30 days before acute rejection is confirmed by biopsy, and 29 to 16 days before acute rejection is confirmed by biopsy. In this way, acute rejection can be predicted at least about 3 months to about two weeks before it happens. Therefore, this mRNA profile analysis can be a new non-invasive "gold standard" to replace and/or supplement an invasive allograft biopsy.

If there is an increase in the select proteins, the patient can be informed that there is increased risk of developing transplant rejection. The increased risk varies in different patients, and the organ transplanted. Generally, the increased risk for developing acute rejection is at least about 25%, at least about 50%, at least about 75%, or at least about 90%, or at least about 99% or at least about 100%.

When the transplanted organ is a kidney, the method can further comprise determining the patient's serum creatinine protein level. The determination of the level of serum creatinine can be made by any method known to those skilled in the art. The next step in this embodiment may comprise correlating the level of serum creatinine in peripheral blood with predicting acute rejection and eventual loss of the transplanted organ. A significantly greater level of serum creatinine in peripheral blood and increased levels of the biomarkers perforin, granzyme B, IP-10, CD103, PI-9, CXCR3, CD3 and/or FoxP3 in urine correlates with acute rejection and may also increase risk of loss of the transplanted kidney.

Generally, the level of serum creatinine in peripheral blood is considered to be significantly greater if the level is at least about 25% greater than the level of creatinine in a control sample. Alternatively, commercial kits can be utilized to test creatinine. An example of a commercial kit for determining creatinine level is the QuantiChrom® Creatinine Assay Kit from BioAssay Systems (Hayward, Calif.).

In this embodiment, a control sample is typically the level of serum creatinine in peripheral blood of a healthy person or a person with a well-functioning (e.g., stable) transplant. For example, the normal level of serum creatinine in a healthy person or a person with a well-functioning transplant is generally about 0.8-1.6 milligrams/deciliter. In either case, the person may be the patient or a person different from the patient.

It is not necessary to determine the level of creatinine in a control sample every time the method is conducted. For example, the serum creatinine level from the patient can be compared to that of one or more previously determined control samples or to a level recognized by the physician or clinician conducting the method, or by a consensus of medical and/or clinical practitioners.

In another embodiment, the method further comprises informing the patient whether the patient will have acute rejection. If so, the patient can then be prescribed and/or administered a treatment to delay rejection of the transplanted organ. Such treatment can include increased or decreased dose of an anti-rejection agent or an anti-rejection agent can be added. Anti-rejection agents, include for example, azathioprine, cyclosporine, FK506, tacrolimus, mycophenolate mofetil, anti-CD25 antibody, antithymocyte globulin, rapamycin, ACE inhibitors, perillyl alcohol, anti-CTLA4 antibody, anti-CD40L antibody, anti-thrombin III, tissue plasminogen activator, antioxidants, anti-CD154, anti-CD3 antibody, thymoglobin, OKT3, corticosteroid, or a combination thereof.

For example, if acute rejection is predicted, a steroid pulse therapy can be started and may include the administration for three to six days of a high dose corticosteroid (e.g., greater than 100 mg). An antibody can be added. An example of an antibody therapy includes the administration for seven to fourteen days of the polyclonal antibody Thymoglobin or the monoclonal antibody, OKT3.

Another example of a treatment that can be administered is plasmapheresis. Plasmapheresis is a process in which the fluid part of the blood (i.e., plasma) is removed from blood cells. Typically, the plasma is removed by a device known as a cell separator. The cells are generally returned to the person undergoing treatment, while the plasma, which contains antibodies, is discarded.

In some embodiments, there is a method for predicting acute rejection using log-transformed mRNA levels of the urine sample that are determined by combinations of log transformed, normalized mRNA levels using a logistic regression model of perforin and PI-9, which predict acute rejection of the transplanted organ within about 90 to about 60 days after the urine sample is tested. In some embodiments, the log-transformed mRNA levels of the urine sample are determined by combinations of log transformed, normalized mRNA levels using a logistic regression model of perforin, IP-10, CXCR3 and FoxP3, which predict acute rejection of the transplanted organ in about 59 to about 30 days after the urine sample is tested. In some embodiments, the log-transformed mRNA levels of the urine sample are determined by combinations of log transformed, normalized mRNA of perforin, PI-9, IP-10, CXCR3, CD3 and granzyme B, which predict acute rejection of the transplanted organ in about 29 to about 15 days after the urine sample is tested.

Kits

In certain embodiments, kits are provided. Commercially available kits for use in these methods are, in view of this specification, known to those of skill in the art. In general, kits will comprise a detection reagent that is suitable for detecting the presence of a polypeptide or nucleic acid, or mRNA of interest.

In another embodiment, there is a panel of probe sets. Preferred probe sets are designed to detect expression of one or more genes and provide information about the rejection of a graft. Preferred probe sets comprise probes or primers (labeled (e.g., fluorescer, quencher, etc.) and unlabeled) that are useful for the detection of at least at least three genes selected from the group consisting of perforin, granzyme B, IP-10, CD3, FoxP3, CXCR3, CD103, PI-9, or TGF-$\beta$1 mentioned in Table 3. Particularly preferred probe sets will comprise probes useful for the detection of at least one, two, three, four, five, six, seven, eight, or nine genes belonging to any of the genes listed in Table 3. Probe sets are particularly useful because they are smaller and cheaper than probe sets that are intended to detect as many genes as possible in a particular genome. The probe sets are targeted at the detection of gene transcripts that are informative about acute rejection. Probe sets may also comprise a large or small number of probes that detect gene transcripts that are not informative about transplant rejection. Such probes are useful as controls and for normalization (e.g., 18S rRNA—SEQ ID NOS: 28-30). Probe sets may be a dry mixture or a mixture in solution. In some embodiments, probe sets can be affixed to a solid substrate to form an array of probes. It is anticipated that probe sets may also be useful for multiplex PCR. The probes may be nucleic acids (e.g., DNA, RNA, chemically modified forms of DNA and RNA), or PNA, or any other polymeric compound capable of specifically interacting with the desired nucleic acid sequences.

It is contemplated that kits may be designed for isolating and/or detecting mRNA in essentially any sample (e.g., urine, blood, etc.), and a wide variety of reagents and methods are, in view of this specification, known in the art.

For example, QIAGEN manufactures a number of commercially available kits for RNA isolation, including RNEASY. Total RNA System (involving binding total RNA to a silica-gel-based membrane and spinning the RNA); OLIGOTEX®. mRNA kits (utilizing spherical latex particles); and QIAGEN total RNA kit for In Vitro Transcripts and RNA clean-up.

In one embodiment, shown in Table 3, quantifying cDNA (obtained by reverse transcribing the mRNA of perforin, granzyme B, IP-10, CD3, FoxP3, CXCR3, CD103, PI-9, or TGF-$\beta$1) using a fluorescence based real-time detection method, such as the ABI PRISM 7500 Sequence Detection System (TaqMan®) commercially available from Applied Biosystems, (Foster City, Calif.) is used. In general, in the TaqMan® assay, 5' nuclease assays employ oligonucleotide probes labeled with at least one fluorescer and at least one quencher (e.g., SEQ ID NO. 3). Prior to cleavage of the probe, the fluorescer excites the quencher(s) rather than producing a detectable fluorescence emission. The oligonucleotide probe hybridizes to a target oligonucleotide sequence for amplification in PCR. The nuclease activity of the polymerase used to catalyze the amplification of the primers (SEQ ID NOS. 1-2) of the target sequence serves to cleave the probe, thereby causing at least one fluorescer to be spatially separated from the quencher so that the signal from the fluorescer is no longer quenched. A change in fluorescence of the fluorescer and/or a change in fluorescence of the quencher due to the oligonucleotide probe being digested is used to indicate the amplification of the target oligonucleotide sequence. Although the primers and probes are specifically described in Table 3 (SEQ ID NOS: 1-30), other suitable primers and probes can be designed using techniques well-known to those of skill in the art.

In other embodiments, kits may comprise probe sets, which may be affixed to a solid surface to form a customized array. In certain embodiments, kits may comprise any of the following components: materials for obtaining a sample, enzymes, buffers and primers for amplifying certain genes, materials for labeling nucleic acids, microarrays, a microarray reader, competitor nucleic acids, housekeeping gene for normalization, control nucleic acids, antibodies for detecting proteins among many other possible components.

In further embodiments, kits may comprise a urine collection system. Urine collection systems may comprise essentially any material useful for obtaining and/or holding a urine sample. Urine collection systems may include, for example, tubing, a beaker, a flask, a test tube or a container with a lid (e.g., a plastic container with a snap-on or screw top lid).

In certain embodiments, kits may also comprise a urine presentation system. A urine presentation system may comprise essentially any material that is useful for presenting the urine to be contacted with the appropriate detection or purification reagents. A urine presentation system may comprise, for example, a sample well, which may be part of a multi-well plate, a petri dish, a filter (e.g., paper, nylon, nitrocellulose, PVDF, cellulose, phosphocellulose, or other fibrous surface), a microchannel (which may be part of a microchannel array or a microfluidics device), a small tube such as a thin-walled PCR tube or a 1.5 ml plastic tube, a microarray to which urine or material obtained from urine may be applied, a capillary tube or a flat or curved surface with detection reagent adhered thereto, or a flat or curved surface with material that adheres to proteins or nucleic acids present in the urine sample.

Kits may also comprise a sample preparation system. A sample preparation system comprises, generally, any materials or substances that are useful in preparing the urine sample to be contacted with the detection reagents. For example, a sample preparation system may comprise materials for separating urine sediments from the fluids, such as centrifuge tube, a microcentrifuge, a filter (optionally fitted to a tube designed to permit a pressure gradient to be established across the filter), buffers, precipitating agents for precipitating either wanted or unwanted materials, chelators, cell lysis reagents etc. It is anticipated that collection, presentation and preparation systems may be combined in various ways. For example, a filter may be used to separate urine sediments from the fluids, and the filter may be coated with antibodies suitable for specifically detecting the desired proteins. One of skill in the art would, in view of this specification, readily understand many combinations of components that a kit of the invention may comprise.

Having now generally described the invention, the same may be more readily understood through the following reference to the following examples, which are provided by way of illustration and are not intended to limit the present invention unless specified.

The Examples below describe the experimental protocols used to develop the anticipatory and diagnostic urinary cell mRNA expression signatures.

EXAMPLES

The inventors report here the results of a multi-center prospective blinded study to confirm the findings that molecular analysis of urine cells that are analyzed in a central lab, and provide a reliable set of biomarkers that are compatible with the local diagnosis of acute cellular rejection (ACR). The results demonstrate that mRNA profiling of the urine samples of kidney transplant recipients is predictive and diagnostic of the development of allograft rejection. The inventors further show that preemptive anti-rejection therapy based on these molecular predictors of rejection will improve graft outcomes.

Example 1

In the cooperative clinical trial conducted between July, 2006 and January, 2008, a total of 497 renal allograft recipients were recruited from the following participating centers: Northwestern (n=145); Cornell (n=122); Penn (n=120); Columbia (n=76); and University of Wisconsin (n=34). Urine, blood, and biopsy samples were collected during the first 12 months of transplantation as per the protocol. The recipients are to be followed up to 48 months post transplant; during this time clinical data that is related to the functional status of the allograft is collected, and any association between gene expression profiles and allograft function identified.

As of December 2008, 4218 urine samples and 318 peripheral blood samples were collected. Urine specimens collected at scheduled visits and at the time of kidney biopsies, were centrifuged and cell pellets were shipped to the Cornell PCR Core blinded to clinical information and biopsy diagnosis. A quantitative PCR assay was used to measure mRNA copy numbers and 18s rRNA copy number (housekeeping gene). As of this date, we have extracted RNA that met RNA quality parameters from 87% of the specimens. A NIH-sponsored Scientific and Clinical Coordinating Center performed data collection, coordination and independent statistical analyses.

Results as of November 2009: Among the 2076 urine specimens with mRNA profiling, 1843 were from patients who did not require biopsy during the post-transplantation follow-up; 155 from patients with biopsies with no rejection; 43 from patients with Banff grade IA or higher (ACR) biopsies; 16 from patients with borderline changes; 8 from patients with AMR; 11 other. Data analysis restricted to those who underwent biopsies demonstrated that 18s-normalized urinary cell levels of perforin ($P<0.0001$, Mann-Whitney test), granzyme B ($<0001$), CD3 ($<0.0001$), IP-10 ($<0.0001$), CD103 (0.002), and Foxp3 (0.002) were higher in the 43 samples from patients with ACR compared to the 155 samples from patients with no rejection (See FIGS. 1-4). Data analysis that included all 2076 urine cell mRNA profiles demonstrated that urinary cell levels of perforin ($<0.0001$), granzyme B ($<0.0001$), CD3 ($<0.0001$), IP-10

Figure 6:
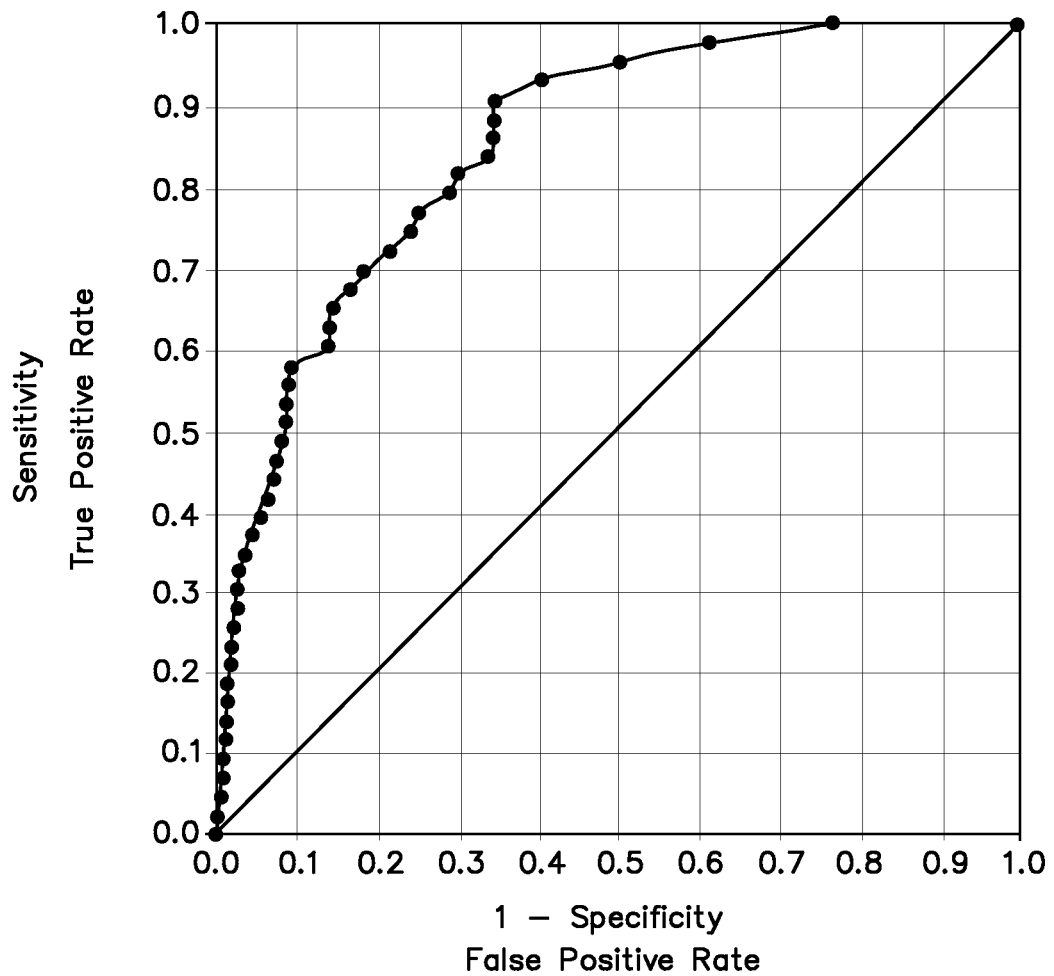
FIG. 6. Receiver Operating Characteristic Curve analysis for Acute Cellular Rejection. Predictors: a weighted combination of urinary cell levels of mRNA for perforin, IP-10, Foxp3 and TGF-beta-1 is diagnostic of acute cellular rejection with a sensitivity of about 91% and a specificity of about 66%. The area under the curve (AUC)=0.84 (95% CI: 0.79-0.90).

(<0.0001), CD103 (0.004), and Foxp3 (0.02) were higher in the 43 samples from patients with ACR compared to the 2033 samples from patients without ACR (See FIGS. 1-3, 5). As shown in FIG. 6 and Table 1 Receiver Operating Characteristic Curve analysis of a weighted combination of log transformed, 18s rRNA normalized mRNA levels of perform, IP-10, Foxp3 and TGF beta1, with weights based on a logistic regression model, demonstrated that a single urine specimen is diagnostic of ACR (86% sensitivity; 70% specificity; AUC: 0.85, 95% CI: 0.80-0.90).

TABLE 1

| | Odds Ratio Estimates | |
| Effect | Point Estimate | 95% Wald Confidence Limits |
| --- | --- | --- |
| ln_Perf | 2.076 | 1.595   2.703 |
| ln_IP10 | 1.253 | 1.045   1.502 |
| ln_TGFb 1 | 0.766 | 0.609   0.963 |
| lw_Foxp3 | 2.532 | 1.098   5.842 |
| z_Foxp3 | 3.882 | 1.209   12.462 |

A Noninvasive Method to Anticipate Acute Cellular Rejection of Human Kidney Transplants The following primary hypothesis was also tested: sequential measurements of urinary cell mRNA profiles are predictive of acute rejection in the near future. We prospectively enrolled 497 adult renal allograft recipients. Urine specimens were collected at scheduled visits and were centrifuged to prepare cell pellets. Total RNA was isolated from the cell pellets and quantitative PCR assays, developed and validated in the investigator's laboratory, was used to measure copy numbers of pre-specified mRNAs. A total of 2076 urine specimens where mRNA profiles that passed quality control parameters were available for data analyses. Among the 2076 urine specimens, 1843 were from patients who did not require biopsy during the post-transplantation follow-up; 155 were from patients with biopsies with no rejection; 43 from patients with Banff grade IA or higher (ACR) biopsies; 16 from patients with borderline changes; 8 from patients with AMR; 11 other. The mRNA levels were screened using univariate t-tests and the candidate genes were then included in a stepwise logistic regression model predicting presence/absence of ACR from the mRNA predictors (9). The mRNA combinations predictive of ACR 90 to 60 days (area under the curve [AUC]: 0.88; P<0.0001), 59 to 30 days (AUC: 0.88; P<0.0001); and 29 to 16 days (AUC: 0.93; P<0.0001) prior to the biopsy identification of ACR are shown in Table 2. Our data demonstrates that mRNA profiles of longitudinally collected urine specimens predict the development of future ACR with a high degree of accuracy.

TABLE 2

Urinary Cell mRNA Expression Signatures Predictive of Future Acute Cellular Rejection (ACR)*

| 90 to 60 Days Prior to Biopsy Diagnosis of ACR | 59 to 30 Days Prior to Biopsy Diagnosis of ACR | 29 to 16 days Prior to Biopsy Diagnosis of ACR |
| --- | --- | --- |
| Perforin | Perforin | Perforin |
| PI-9 | IP10 | PI-9 |
| | CXCR3 | IP10 |
| | Foxp3 | CXCR3 |
| | | CD3 |
| | | Granzyme B |
| AUC = 0.88 | AUC = 0.88 | AUC = 0.93 |
| P < 0.0001 | P < 0.0001 | P < 0.0001 |

Clinical Protocol

The levels of specific mRNAs were measured in urinary cells obtained during the first 12 months after kidney transplantation. The study was designed to investigate whether molecular profiling is predictive and reliable. The study was also designed to investigate whether the results are independent of the type of induction and maintenance of immunosuppression.

The prospective cohort study performed was comprised of renal allograft recipients (0-80 yrs) of all genders and race, and willing to undergo urine collection at days 3, 7, 15, 30 and months 2-6, 9 and 12 post transplantation. The study included all patients undergoing kidney transplantation with a live or deceased donor allograft at the participating centers.

Study Design

This was an observational, uncontrolled and non-randomized study in which all deceased donor and living donor kidney allograft recipients at all participating centers were eligible for enrollment. The two major aims were to determine whether mRNA profiles of sequential urine specimens predict the development of rejection in the future and whether the MRNA profile of a urine sample could diagnose acute cellular rejection.

This was a non-blinded study. However, the treating physician was not notified of the results of the urine mRNA profiling studies. This was to assure that the treatment modality will be based on standard of care practice (i.e., kidney biopsy results), and will not be affected by the results of the urinary mRNA profiles.

Data analyses included examination of whether mRNA profiles of sequential urine specimens predict the development of rejection.

Kidney recipients were consented for the study and asked to donate urine samples at predetermined intervals during the first 12 months after the procedure. Additional urine samples were collected prior to standard of care kidney biopsies, and at two weeks following treatment of biopsy-proven acute rejection.

There were no stopping rules; however, patients were not followed in the event of graft loss.

Selection and Withdrawal of Participants

Inclusion Criteria

Patients who meet all of the following criteria were enrolled as study participants:

Male and female recipients of all races, 0-80 years of age.

Patients undergoing primary or re-do deceased-donor or living donor kidney transplantation.

Ability to provide informed consent.

Exclusion Criteria

Patients who meet any of these criteria were not eligible for enrollment as study participants:

Patients undergoing combined organ transplantation.

Patients who are recipients of previous non-renal solid organ and/or islet cell transplantation.

HCV or HIV infection.

Inability or unwillingness of a participant to provide informed consent.

Participant Withdrawal Criteria

Premature Termination from the Study

Participants prematurely terminated from the study for the following reasons:

The participant electing to withdraw consent from all future study activities, including follow-up.

The participant "lost to follow-up" (i.e., no further follow-up was possible because attempts to reestablish contact with the participant have failed).

The participant died.

Loss of graft.

Enrollment

The research study was explained in lay terms to each potential research participant. The participant signed an informed consent form before undergoing any screening study procedures. Participants who were deemed eligible for the study were enrolled and assigned a unique participant number.

In this cooperative clinical trial conducted between July, 2006 and January, 2008, a total of 497 renal allograft recipients were recruited from the following participating centers: Northwestern (n=145); Cornell (n=122); Penn (n=120); Columbia (n=76); and University of Wisconsin (n=34). Urine samples were collected during the first 12 months of transplantation as per the protocol specified below, centrifuged and cell pellets were shipped to the Cornell gene expression core for RNA isolation, reverse transcription to cDNA, pre-amplification with gene specific primer pairs and measurement of mRNA levels with real time quantitative PCR assays.

Baseline Visit (Screening and Enrollment)

Subjects were enrolled and consented by the attending physician or designee. For deceased-donor recipients, the baseline visit occurred prior to transplant or 48-72 hours post-transplant in the absence of heavy narcotics. For living donor recipients, the baseline visit occurred no more than two months prior to transplantation or 48-72 hours post-transplant in the absence of heavy narcotics.

During the screening visit a medical history and physical examination was performed and the subject's demographic information were collected.

Follow-Up Visits

The participants provided urine samples at baseline, post-transplant days 3, 7, 15, 30, months 2-6, 9, and 12 months. Additional visits occurred when a participant was admitted for work up of abnormal kidney function. During these visits, additional urine was collected prior to the biopsy and 14 days after treatment.

Safety Monitoring

This study involved minimal active intervention outside of the normal standard of care for the participant. Thus, for this study, reportable adverse events were limited, and the investigators were instructed to adhere to the requirements and guidelines for adverse event and serious adverse event reporting.

Identification and Access to Source Data

Identifying Source Data

The investigator was required to keep accurate records to ensure that the conduct of the study is fully documented. The results of all clinical and clinical laboratory evaluations were maintained in the participant's medical records and the data were to be transferred to clinical case report forms (CRFs). Safety data were recorded on CRFs specifically designed for this purpose. Any serious adverse events (SAEs) were reported on an SAE report form as well as on individual CRFs. All data were to be reviewed periodically by the Data and Safety Monitoring Board (DSMB) and Institutional Review Board (IRB). The DSMB and/or the IRB had the authority to withdraw any participants and/or terminate the study because of safety findings.

Permitting Access to Source Data

The investigational site participating in this study was asked to maintain the highest degree of confidentiality permitted for the clinical and research information obtained from the participants in this clinical trial. Medical and research records were maintained at each site in the strictest confidence. However, as a part of the quality assurance and legal responsibilities of an investigation, the investigational site was required to permit authorized representatives of the sponsor(s) and health authorities to examine (and when required by applicable law, to copy) clinical records for the purpose of quality assurance reviews, audits, and evaluations of the study safety and progress. Unless required by the laws that permit copying of records, only the coded identity associated with documents or with other participant data were copied (and all personally identifying information must be obscured). Authorized representatives as noted above were bound to maintain the strict confidentiality of medical and research information that is linked to identify individuals. The investigational site was notified before auditing visits occur.

Quality Control and Quality Assurance

The investigator was required to keep accurate records to ensure that the conduct of the study was fully documented.

The sponsor was responsible for regularly reviewing the conduct of the trial, for verifying adherence to the protocol, and for confirming the completeness, consistency, and accuracy of all documented data.

Data Handling

The investigator was required to ensure that a case report form (CRF) was completed for every participant entered in the trial. The data were to be verified by a series of computerized edit checks, and all relevant data queries to be resolved regularly. When the CRFs were complete, they were reviewed and signed by the investigator and returned to the sponsor or designees. All data from the original signed CRF were to be entered in the database, and a comparison program was to be run again. All discrepancies were to be reviewed, and any resulting queries were to be resolved with the investigator and amended in the database. All elements of data entry (i.e., time, date, verbatim text, and the name of the person performing the data entry) were to be recorded in an electronic audit trail to allow all data changes in the database to be monitored and maintained in accordance with federal regulations.

Ethical Considerations and Compliance with Good Clinical Practice

Statement of Compliance

This clinical study was conducted using good clinical practice (GCP), as delineated in *Guidance for Industry: E6 Good Clinical Practice Consolidated Guidance*, and according to the criteria specified in this study protocol. Before study initiation, the protocol and the informed consent documents were reviewed and approved by an appropriate EC or IRB. Any amendments to the protocol or to the consent materials were approved before they are implemented.

Privacy and Confidentiality

A participant's privacy and confidentiality was to be respected throughout the study. Each participant was assigned a sequential identification number, and these numbers rather than names were used to collect, store, and report participant information.

Example 2

Measurement of Messenger RNA Levels in Urine

Isolation of Total RNA from Urine:

Urine was centrifuged at 2,000 g for 30 minutes. RNA was extracted from the pellet with use of a commercial kit. The yield and purity of total RNA isolated from the biologic specimens was measured using a NanoDrop ND-1000® spectrophotometer (NanoDrop Products, Wilmington, Del., USA).

Reverse Transcription for mRNA Profiling:

cDNA for mRNA profiling were prepared using TaqMan® reverse transcription reagents (Applied Biosystems, Foster City, Calif.).

Quantification of mRNAs Using Pre-Amplification Enhanced Real-Time Quantitative PCR Assay:

We have successfully adapted the TaqMan® real-time quantitative PCR assay and developed a pre-amplification enhanced real-time quantitative PCR assay that allows absolute quantification of a large panel of mRNAs from minute amounts of cDNA (e.g., 20 different mRNAs from 3 μl cDNA at 1 μg of total RNA in 1000). This assay is comprised of two sequential steps; in the first step, the pre-amplification reaction is set up for each sample in a 0.2 ml PCR tube with a final reaction volume of 10 μl containing 3.0 μl cDNA (from reverse transcription of 1 μg total RNA in 1000, 1.0 μl 10× buffer, 0.6 μl MgCl2 (25 mM), 0.4 μl 4× dNTP (10 mM each), 0.4 μl Ampli-Taq gold (5U/μl), 0.15 μl primer mix per gene (50 μM sense and 50 μM antisense primer) and water to final volume of 10 μl. Following vortexing, the PCR is set up using a Veriti thermal cycler and the 10-cycle PCR reaction profile consists of an initial hold at 95° C. for 10 min, denaturing at 95° C. for 10 seconds and primer annealing and extension at 60° C. for 1 min. At the end of 10 cycles, 90 μl of TE buffer is added to the PCR reaction and 2.5 μl of diluted PCR amplicon is used for quantification of mRNA using the real-time quantitative PCR assay.

The levels of mRNAs were measured using an ABI Prism 7500 Fast detection system (Applied Biosystems). PCR reaction for each sample was set up in duplicate as a 20 μl reaction volume using 10.0 μl 2× Fast TaqMan PCR Master Mix, 2.5 μl pre-amplified template cDNA, 0.15 μl primers (sense primer and antisense primer, 50 μM each), 0.05 μl probe (100 μM) and 7.34 μl of water. The PCR amplification protocol consisted of an initial hold at 95° C. for 20 seconds and 40 cycles of denaturing at 95° C. for 3.0 seconds and primer annealing and extension at 60° C. for 30 seconds. mRNA levels were calculated using our previously described synthetic amplicon incorporated standard curve method, and mRNA copy numbers were normalized using 18S rRNA copy numbers (mRNA copies in one μg RNA/18S rRNA copies in one fg RNA). Oligonucleotide primers and fluorogenic TaqMan® probes for this study have been designed and validated and the sequences of the primers and the probes used are listed in Table 3.

Our primers were designed to span an intron, thereby avoiding any genomic (DNA) contribution to the mRNA copy number. The probes were labeled with 6-carboxy-fluorescein at the 5' end and 6-carboxy-tetramethylrodamine or minor groove binder (MGB) at the 3' end. FAM functioned as the reporter dye and TAMRA as the quencher dye. In our studies, 18S rRNA was used as the housekeeping gene and used to normalize mRNA levels.

mRNA Profiling:

Levels of urinary cell mRNA for granzyme B, perforin, PI-9, CD3ε, IP-10, CXCR3, FoxP3, TGF-β1 and CD103 and the reference gene 18S rRNA were measured using our pre-amplification enhanced real-time quantitative PCR assay.

TABLE 3

Oligonucleotide primers and probes used in real time quantitative polymerase chain reaction assays for the quantification of mRNAs.

| | Gene | Accession number | Sequence | Location |
|---|---|---|---|---|
| SEQ ID NO. 1 | Granzyme B | J04071 | Sense: 5'-GCGAATCTGACTTACGCCATTATT-3' | 534-557 |
| SEQ ID NO. 2 | | | Antisense: 5'-CAAGAGGGCCTCCAGAGTCC-3' | 638-619 |
| SEQ ID NO. 3 | | | Probe: 5'-FAM-CCCACGCACAACTCAATGGTACTGTCG-TAMRA-3' | 559-585 |
| SEQ ID NO. 4 | Perforin | M28393 | Sense: 5'-GGACCAGTACAGCTTCAGCACTG-3' | 492-514 |
| SEQ ID NO. 5 | | | Antisense: 5'-GCCCTCTTGAAGTCAGGGTG-3' | 587-568 |
| SEQ ID NO. 6 | | | Probe: 5'-FAM-TGCCGCTTCTACAGTTTCCATGTGGTACAC-TAMRA-3' | 526-555 |
| SEQ ID NO. 7 | PI-9 | NM_004155 | Sense: 5'-'TCAACACCTGGGTCTCAAAAAA-3' | 508-529 |
| SEQ ID NO. 8 | | | Antisense: 5'- CAGCCTGGTTTCTGCATCAA-3' | 590-571 |
| SEQ ID NO. 9 | | | Probe: 5'-FAM-AGC TAC CCG GCA ACA ACT CTT CAA TTT TAC CT-TAMRA -3' | 536-567 |
| SEQ ID NO. 10 | FoxP3 | NM_014009 | Sense 5'-GAGAAGCTGAGTGCCATGCA-3' | 939-958 |
| SEQ ID NO. 11 | | | Antisense 5-GGAGCCCTTGTCGGATGAT-3' | 1025-1007 |
| SEQ ID NO. 12 | | | Probe 5'-FAM-TGCCATTTTCCCAGCCAGGTGG-TAMRA-3' | 962-983 |

TABLE 3-continued

Oligonucleotide primers and probes used in real time quantitative polymerase chain reaction assays for the quantification of mRNAs.

| | Gene | Accession number | Sequence | Location |
|---|---|---|---|---|
| SEQ ID NO. 13 | IP10 | NM_001565 | Sense: 5'-ATTTTGTCCACGTGTTGAGATCA-3' | 231-253 |
| SEQ ID NO. 14 | | | Antisense: 5'-TGGCCTTCGATTCTGGATTC-3' | 310-291 |
| SEQ ID NO. 15 | | | Probe: 5'-FAM-GACATCTCTTCTCACCCTTCTTTTTCATTGTAGCA-TAMRA-3' | 289-255 |
| SEQ ID NO. 16 | CXCR3 | NM_001504 | Sense: 5'-ACCCAGCAGCCAGAGCAC-3' | 41-58 |
| SEQ ID NO. 17 | | | Antisense: 5'-CAACCTCGGCGTCATTTAGC-3' | 117-98 |
| SEQ ID NO. 18 | | | Probe: 5'-FAM-CTTGGTGGTCACTCACCTCAAGGACCAT-TAMRA-3' | 69-96 |
| SEQ ID NO. 19 | CD3 | NM_000733 | Sense: 5'-AAGAAATGGGTGGTATTACACAGACA-3' | 131-156 |
| SEQ ID NO. 20 | | | Antisense: 5'-TGCCATAGTATTTCAGATCCAGGAT-3' | 233-209 |
| SEQ ID NO. 21 | | | Probe: 5'-FAM-CCATCTCTGGAACCACAGTAATATTGACATGCC-TAMRA-3' | 170-202 |
| SEQ ID NO. 22 | TGFβ1 | NM_000660 | Sense: 5'-GCGTGCTAATGGTGGAAACC-3' | 1170-1189 |
| SEQ ID NO. 23 | | | Antisense: 5'-CGGAGCTCTGATGTGTTGAAGA-3' | 1263-1242 |
| SEQ ID NO. 24 | | | Probe: 5'-FAM-ACAACGAAATCTATGACAAGTTCAAGCAGAGTACACA-TAMRA-3' | 1191-1227 |
| SEQ ID NO. 25 | CD103 | XM_008508 | Sense: 5'-CGTGCTCAGCTCCCTTCTG-3' | 211-229 |
| SEQ ID NO. 26 | | | Antisense: 5'-CCTGGTGTCCTCTTGGTTCTG-3' | 297-277 |
| SEQ ID NO. 27 | | | Probe: 5'-FAM-ACCAAGACCCCAGCACCAACCATACCT-TAMRA-3' | 231-257 |
| SEQ ID NO. 28 | 18S rRNA | K03432 | Sense: 5'-GCCCGAAGCGTTTACTTTGA-3' | 929-948 |
| SEQ ID NO. 29 | | | Antisense: 5'-TCCATTATTCCTAGCTGCGGTATC-3' | 1009-986 |
| SEQ ID NO. 30 | | | Probe: 5' -FAM-AAAGCAGGCCCGAGCCGCC-TAMRA-3' | 965-983 |

Statistical Analysis

The 18S-normalized mRNA levels deviated from a normal distribution, but a log transformation substantially reduced the positive skew. The mRNA levels were screened using univariate t-tests and the candidate genes were then included in a stepwise logistic regression model predicting presence/absence of ACR from the mRNA predictors (9). We used a conventional receiver-operating-characteristic (ROC) curve to calculate the area under the curve (AUC).

Results

A total of 2076 mRNA profiles that passed quality control parameters were available for data analyses. Among the 2076 urine specimens successfully profiled, 1843 were from patients who did not require biopsy during the post-transplantation follow-up; 155 were from patients with biopsies with no rejection; 43 from patients with Banff grade IA or higher (ACR) biopsies; 16 from patients with borderline changes; 8 from patients with AMR; 11 other.

The mRNA profiles of earlier urine samples of allograft patients who had biopsy confirmed ACR were then analyzed for predictors of future ACR. A combination of levels of perform and PI-9, measured in urine specimens collected 90 to 60 days prior to biopsy confirmed ACR, accurately predicted the future development of ACR, and ROC curve analysis yielded an AUC of 0.88 ($P<0.0001$).

A combination of levels of perforin, IP10, CXCR3 and Foxp3, measured in urine specimens collected 59 to 30 days prior to biopsy confirmed ACR, accurately predicted the future development of ACR, and ROC curve analysis yielded an AUC of 0.88 ($P<0.0001$). A combination of levels of perforin, PI-9, IP10, CXCR3, CD3 and granzyme B, measured in urine specimens collected 29 to 16 days prior to biopsy confirmed ACR, accurately predicted the future development of ACR, and the area under the curve was 0.93 (P<0.0001) by receiver operating characteristic (ROC) curve analysis.

The references listed below are herein incorporated by reference into the present disclosure.

REFERENCES

1. Anglicheau D, Suthanthiran M. Noninvasive prediction of organ graft rejection and outcome using gene expression patterns. Transplantation 2008; 86(2):192-199.
2. Dadhania D, Muthukumar T, Ding R, Li B, Hartono C, Serur D et al. Molecular signatures of urinary cells distinguish acute rejection of renal allografts from urinary tract infection. Transplantation 2003; 75(10):1752-1754.
3. Ding R, Li B, Muthukumar T, Dadhania D, Medeiros M, Hartono C et al. CD103 mRNA levels in urinary cells predict acute rejection of renal allografts. Transplantation 2003; 75(8):1307-1312.
4. Ding R, Medeiros M, Dadhania D, Muthukumar T, Kracker D, Kong J M et al. Noninvasive diagnosis of BK virus nephritis by measurement of messenger RNA for BK virus VP1 in urine. Transplantation 2002; 74(7):987-994.
5. Li B, Hartono C, Ding R, Sharma V K, Ramaswamy R, Qian B et al. Noninvasive diagnosis of renal-allograft rejection by measurement of messenger RNA for perform and granzyme B in urine. N Engl J Med 2001; 344(13):947-954.
6. Muthukumar T, Dadhania D, Ding R, Snopkowski C, Naqvi R, Lee J B et al. Messenger RNA for FOXP3 in the urine of renal-allograft recipients. N Engl J Med 2005; 353(22):2342-2351.
7. Muthukumar T, Ding R, Dadhania D, Medeiros M, Li B, Sharma V K et al. Serine proteinase inhibitor-9, an endogenous blocker of granzyme B/perforin lytic pathway, is hyperexpressed during acute rejection of renal allografts. Transplantation 2003; 75(9):1565-1570.
8. Tatapudi R R, Muthukumar T, Dadhania D, Ding R, Li B, Sharma V K et al. Noninvasive detection of renal allograft inflammation by measurements of mRNA for IP-10 and CXCR3 in urine. Kidney Int 2004; 65(6):2390-2397.
9. Afaneh C, Muthukumar T, Lubetzky M, Ding R, Snopkowski C, Sharma V K, Seshan S, Dadhania D, Schwartz J E, Suthanthiran M. Urinary Cell Levels of mRNA for OX40, OX40L, PD-1, PD-L1, or PD-L2 and Acute Rejection of Human Renal Allografts. Transplantation. 2010 Nov. 12. [Epub ahead of print] PubMed PMID: 21079547.
10. U.S. Pat. No. 6,187,534, Methods of Evaluating Transplant Rejection
11. U.S. Pat. No. 6,900,015, Methods of Evaluating Transplant Rejection
12. US20080131441, Methods of Using FOXP3 Levels to Predict the Outcome of Organs Undergoing Acute Rejection The Abstract is submitted with the understanding that it will not be used to interpret or limit the scope or meaning of the claims.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

The material in ASCII text file SEQUENCE_ST25.txt, created Feb. 21, 2011 and 5.67 KB in size, is hereby incorporated by reference

What is claimed is:

1. A method comprising:
   obtaining a urinary cell sample from a human patient with a renal allograft but without acute cellular rejection of the allograft;
   quantifying mRNA expression levels of perforin, granzyme B, PI-9, IP-10, CD3, FoxP3, and CXCR3 in the urinary cell sample of the patient;
   comparing the quantified mRNA expression levels in the urinary cell sample to a corresponding baseline level of mRNA expression of perforin, granzyme B, PI-9, IP-10, CD3, FoxP3, and CXCR3 in urinary cells from a healthy subject or a subject with a non-rejecting renal allograft;
   detecting upregulation of mRNA expression of perforin, granzyme B, PI-9, IP-10, CD3, and CXCR3 in the urinary cell sample of the patient and initiating treatment with, or providing a modified dose of, an anti-rejection agent to the patient, or
   detecting upregulation of mRNA expression of perforin, IP-10, FoxP3, and CXCR3 in the urinary cell sample of the patient and initiating treatment with, or providing a modified dose of, an anti-rejection agent to the patient; and
   obtaining an additional urinary cell sample from the patient after said initiating treatment with, or providing a modified dose of, an anti-rejection agent, and quantifying mRNA expression levels of perforin, granzyme B, PI-9, IP-10, CD3, FoxP3, and CXCR3 in the additional urinary cell sample from the patient.

2. The method according to claim 1, further comprising comparing log-transformed mRNA expression levels of perforin, granzyme B, PI-9, CD3, FoxP3, and CXCR3 in a urine cell sample from the patient to corresponding log-transformed baseline levels of mRNA expression of perforin, granzyme B, PI-9, IP-10, CD3, FoxP3, and CXCR3 in urine cells from a healthy subject or a subject with a non-rejecting renal allograft.

3. The method according to claim 2, wherein the log-transformed mRNA levels of perforin, granzyme B, PI-9, IP-10, CD3, FoxP3, and CXCR3 are determined by (i) normalizing mRNA levels to 18S rRNA using a logistic regression model of perforin, granzyme B, PI-9, IP-10, CD3, FoxP3, or CXCR3, or (ii) a weighted combination of at least three log transformed, normalized mRNA levels of perforin, IP-10, FoxP3, granzyme B, PI-9, CD3, or CXCR3 based on a logistic regression model.

4. A method according to claim 1, further comprising diagnosing future acute rejection when upregulation of mRNA levels is detected in the urine cell sample from the patient.

5. A method according to claim 1, wherein the method further comprises determining the patient's serum creatinine level in peripheral blood.

6. A method according to claim 1, wherein the anti-rejection agent is at least one of azathioprine, cyclosporine, FK506, tacrolimus, mycophenolate mofetil, anti-CD25 antibody, antithymocyte globulin, rapamycin, ACE inhibitors, perillyl alcohol, anti-CTLA4 antibody, anti-CD40L antibody, anti-thrombin III, tissue plasminogen activator, anti-oxidants, anti-CD 154, anti-CD3 antibody, thymoglobin, OKT3, corticosteroid, or a combination thereof.

7. The method of claim 1, wherein quantifying mRNA expression levels comprises quantifying mRNA levels using one or more probes or primers selected from the group consisting of SEQ ID NO: 1-21, 28, 29 and 30.

* * * * *

UNITED STATES PATENT AND TRADEMARK OFFICE
CERTIFICATE OF CORRECTION

PATENT NO. : 9,746,479 B2
APPLICATION NO. : 13/583750
DATED : August 29, 2017
INVENTOR(S) : Suthanthiran et al.

Page 1 of 1

It is certified that error appears in the above-identified patent and that said Letters Patent is hereby corrected as shown below:

On the Title Page

On page 2, in Column 1, under "Other Publications", Line 16, delete "arid" and insert --and-- therefor In the Specification In Column 1, Line 13-17, delete "This invention was made with Government support under Grant Number 5U01AI063589-05S1 and 5U01AI063589-05 awarded by National Institute of Allergy and Infectious Diseases. The United States Government has certain rights in the invention." and insert --This invention was made with government support under Grant Number AI063589 awarded by the National Institutes of Health. The Government has certain rights in the invention.-- therefor In the Claims In Column 41, Line 46, in Claim 2, after "PI-9,", insert --IP-10,--

Signed and Sealed this
Twenty-fourth Day of April, 2018

Andrei Iancu
*Director of the United States Patent and Trademark Office*

SEQUENCE LISTING

```
<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: sense primer

<400> SEQUENCE: 1
gcgaatctga cttacgccat tatt                                            24

<210> SEQ ID NO 2
<211> LENGTH: 20
<212> TYPE: DNA
<213> ORGANISM: Artificial Sequence
<220> FEATURE:
<223> OTHER INFORMATION: antisense primer

<400> SEQUENCE: 2
caagagggcc tccagagtcc                                                 20

<210> SEQ ID NO 3
<211> LENGTH: 27
<212> TYPE: DNA
<213> ORGANISM: Artificial Sequence
<220> FEATURE:
<223> OTHER INFORMATION: probe
```

```
<400> SEQUENCE: 3
cccacgcaca actcaatggt actgtcg                                    27

<210> SEQ ID NO 4
<211> LENGTH: 23
<212> TYPE: DNA
<213> ORGANISM: Artificial Sequence
<220> FEATURE:
<223> OTHER INFORMATION: sense primer

<400> SEQUENCE: 4
ggaccagtac agcttcagca ctg                                        23

<210> SEQ ID NO 5
<211> LENGTH: 20
<212> TYPE: DNA
<213> ORGANISM: Artificial Sequence
<220> FEATURE:
<223> OTHER INFORMATION: antisense primer

<400> SEQUENCE: 5
gccctcttga agtcagggtg                                            20

<210> SEQ ID NO 6
<211> LENGTH: 30
<212> TYPE: DNA
<213> ORGANISM: Artificial Sequence
<220> FEATURE:
<223> OTHER INFORMATION: probe

<400> SEQUENCE: 6
tgccgcttct acagtttcca tgtggtacac                                 30

<210> SEQ ID NO 7
<211> LENGTH: 22
<212> TYPE: DNA
<213> ORGANISM: Artificial Sequence
<220> FEATURE:
<223> OTHER INFORMATION: sense primer

<400> SEQUENCE: 7
tcaacacctg ggtctcaaaa aa                                         22

<210> SEQ ID NO 8
<211> LENGTH: 20
<212> TYPE: DNA
<213> ORGANISM: Artificial Sequence
<220> FEATURE:
<223> OTHER INFORMATION: antisense primer

<400> SEQUENCE: 8
cagcctggtt tctgcatcaa                                            20

<210> SEQ ID NO 9
<211> LENGTH: 32
<212> TYPE: DNA
<213> ORGANISM: Artificial Sequence
<220> FEATURE:
<223> OTHER INFORMATION: probe

<400> SEQUENCE: 9
agctacccgg caacaactct tcaattttac ct                              32

<210> SEQ ID NO 10
<211> LENGTH: 20
```

```
<212> TYPE: DNA
<213> ORGANISM: Artificial Sequence
<220> FEATURE:
<223> OTHER INFORMATION: sense primer

<400> SEQUENCE: 10
gagaagctga gtgccatgca                                              20

<210> SEQ ID NO 11
<211> LENGTH: 19
<212> TYPE: DNA
<213> ORGANISM: Artificial Sequence
<220> FEATURE:
<223> OTHER INFORMATION: antisense primer

<400> SEQUENCE: 11
ggagcccttg tcggatgat                                               19

<210> SEQ ID NO 12
<211> LENGTH: 22
<212> TYPE: DNA
<213> ORGANISM: Artificial Sequence
<220> FEATURE:
<223> OTHER INFORMATION: probe

<400> SEQUENCE: 12
tgccattttc ccagccaggt gg                                           22

<210> SEQ ID NO 13
<211> LENGTH: 23
<212> TYPE: DNA
<213> ORGANISM: Artificial Sequence
<220> FEATURE:
<223> OTHER INFORMATION: sense primer

<400> SEQUENCE: 13
attttgtcca cgtgttgaga tca                                          23

<210> SEQ ID NO 14
<211> LENGTH: 20
<212> TYPE: DNA
<213> ORGANISM: Artificial Sequence
<220> FEATURE:
<223> OTHER INFORMATION: antisense primer

<400> SEQUENCE: 14
tggccttcga ttctggattc                                              20

<210> SEQ ID NO 15
<211> LENGTH: 35
<212> TYPE: DNA
<213> ORGANISM: Artificial Sequence
<220> FEATURE:
<223> OTHER INFORMATION: probe

<400> SEQUENCE: 15
gacatctctt ctcacccttc tttttcattg tagca                             35

<210> SEQ ID NO 16
<211> LENGTH: 18
<212> TYPE: DNA
<213> ORGANISM: Artificial Sequence
<220> FEATURE:
<223> OTHER INFORMATION: sense primer

<400> SEQUENCE: 16
```
acccagcagc cagagcac                                                  18

<210> SEQ ID NO 17
<211> LENGTH: 20
<212> TYPE: DNA
<213> ORGANISM: Artificial Sequence
<220> FEATURE:
<223> OTHER INFORMATION: antisense primer

<400> SEQUENCE: 17
caacctcggc gtcatttagc                                                20

<210> SEQ ID NO 18
<211> LENGTH: 28
<212> TYPE: DNA
<213> ORGANISM: Artificial Sequence
<220> FEATURE:
<223> OTHER INFORMATION: probe

<400> SEQUENCE: 18
cttggtggtc actcacctca aggaccat                                       28

<210> SEQ ID NO 19
<211> LENGTH: 26
<212> TYPE: DNA
<213> ORGANISM: Artificial Sequence
<220> FEATURE:
<223> OTHER INFORMATION: sense primer

<400> SEQUENCE: 19
aagaaatggg tggtattaca cagaca                                         26

<210> SEQ ID NO 20
<211> LENGTH: 25
<212> TYPE: DNA
<213> ORGANISM: Artificial Sequence
<220> FEATURE:
<223> OTHER INFORMATION: antisense primer

<400> SEQUENCE: 20
tgccatagta tttcagatcc aggat                                          25

<210> SEQ ID NO 21
<211> LENGTH: 33
<212> TYPE: DNA
<213> ORGANISM: Artificial Sequence
<220> FEATURE:
<223> OTHER INFORMATION: probe

<400> SEQUENCE: 21
ccatctctgg aaccacagta atattgacat gcc                                 33

<210> SEQ ID NO 22
<211> LENGTH: 20
<212> TYPE: DNA
<213> ORGANISM: Artificial Sequence
<220> FEATURE:
<223> OTHER INFORMATION: sense primer

<400> SEQUENCE: 22
gcgtgctaat ggtggaaacc                                                20

<210> SEQ ID NO 23
<211> LENGTH: 22
<212> TYPE: DNA
<213> ORGANISM: Artificial Sequence

```
<220> FEATURE:
<223> OTHER INFORMATION: antisense primer

<400> SEQUENCE: 23
cggagctctg atgtgttgaa ga                                              22

<210> SEQ ID NO 24
<211> LENGTH: 37
<212> TYPE: DNA
<213> ORGANISM: Artificial Sequence
<220> FEATURE:
<223> OTHER INFORMATION: probe

<400> SEQUENCE: 24
acaacgaaat ctatgacaag ttcaagcaga gtacaca                              37

<210> SEQ ID NO 25
<211> LENGTH: 19
<212> TYPE: DNA
<213> ORGANISM: Artificial Sequence
<220> FEATURE:
<223> OTHER INFORMATION: sense primer

<400> SEQUENCE: 25
cgtgctcagc tcccttctg                                                  19

<210> SEQ ID NO 26
<211> LENGTH: 21
<212> TYPE: DNA
<213> ORGANISM: Artificial Sequence
<220> FEATURE:
<223> OTHER INFORMATION: antisense primer

<400> SEQUENCE: 26
cctggtgtcc tcttggttct g                                               21

<210> SEQ ID NO 27
<211> LENGTH: 27
<212> TYPE: DNA
<213> ORGANISM: Artificial Sequence
<220> FEATURE:
<223> OTHER INFORMATION: probe

<400> SEQUENCE: 27
accaagaccc cagcaccaac catacct                                         27

<210> SEQ ID NO 28
<211> LENGTH: 20
<212> TYPE: DNA
<213> ORGANISM: Artificial Sequence
<220> FEATURE:
<223> OTHER INFORMATION: sense primer

<400> SEQUENCE: 28
gcccgaagcg tttactttga                                                 20

<210> SEQ ID NO 29
<211> LENGTH: 24
<212> TYPE: DNA
<213> ORGANISM: Artificial Sequence
<220> FEATURE:
<223> OTHER INFORMATION: antisense primer

<400> SEQUENCE: 29
tccattattc ctagctgcgg tatc                                            24
```

```
<210> SEQ ID NO 30
<211> LENGTH: 19
<212> TYPE: DNA
<213> ORGANISM: Artificial Sequence
<220> FEATURE:
<223> OTHER INFORMATION: probe

<400> SEQUENCE: 30
aaagcaggcc cgagccgcc                                              19
```